(12) United States Patent
Glover, III

(10) Patent No.: US 7,604,943 B2
(45) Date of Patent: *Oct. 20, 2009

(54) SYSTEMS AND METHODS OF ANALYZING NUCLEIC ACID POLYMERS AND RELATED COMPONENTS

(75) Inventor: William Roy Glover, III, North Reading, MA (US)

(73) Assignee: ZS Genetics, Inc., North Reading, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/983,055

(22) Filed: Nov. 6, 2007

(65) Prior Publication Data

US 2008/0199871 A1    Aug. 21, 2008

Related U.S. Application Data

(63) Continuation of application No. 11/181,695, filed on Jul. 14, 2005, now Pat. No. 7,291,468.

(60) Provisional application No. 60/587,997, filed on Jul. 14, 2004.

(51) Int. Cl.
    *C12Q 1/68* (2006.01)
(52) U.S. Cl. ......................................... 435/6
(58) Field of Classification Search ........................ None
    See application file for complete search history.

(56) References Cited

U.S. PATENT DOCUMENTS 6,303,296 B1   10/2001   Bensimon et al.

| | | |
|---|---|---|
| 7,288,379 B2 | 10/2007 | Glover |
| 7,291,467 B2 * | 11/2007 | Glover, III ..................... 435/6 |
| 7,291,468 B2 * | 11/2007 | Glover, III ..................... 435/6 |
| 2002/0086317 A1 | 7/2002 | Nagayama |
| 2004/0038261 A1 | 2/2004 | Nagayama |

FOREIGN PATENT DOCUMENTS

| | | |
|---|---|---|
| DE | 10123443 A1 | 11/2002 |
| EP | 0 429 122 A1 | 5/1991 |
| EP | 0 517 930 A1 | 12/1992 |
| EP | 1 542 009 A1 | 6/2005 |
| WO | WO 95/01559 A2 | 1/1995 |
| WO | WO 95/21939 A1 | 8/1995 |
| WO | WO 01/03833 A1 | 1/2001 |
| WO | WO 2004/097032 A2 | 11/2004 |
| WO | WO 2006/019903 A1 | 2/2006 |
| WO | WO 2006/127736 A2 | 11/2006 |

OTHER PUBLICATIONS

Grant, A.W. et al., "Transmission electron microscopy 'windows' for nanofabricated structures," *Nanotechnology* 2004; 15:1175-1181.
Kasemo, B., "Biological surface science," Surface Science 2002; 500:656-677.
Jaunin, F. et al., "Fine Structural in Situ Analysis of Nascent DNA Movement Following DNA Replication," *Experimental Cell Research* 2000; 260:313-323.
Migheli, A. "Electron Microscopic Detection of DNA Damage Labeled by TUNEL," *Methods in Molecular Biology* 2002; 203:31-39.

* cited by examiner

*Primary Examiner*—James Martinell
(74) *Attorney, Agent, or Firm*—Wolf, Greenfield & Sacks, P.C.

(57) ABSTRACT

Systems and methods of identifying, sequencing and/or detecting nucleic acid polymers, as well as related components (e.g., substrates, software and the like) are disclosed.

47 Claims, 9 Drawing Sheets

US 7,604,943 B2

SYSTEMS AND METHODS OF ANALYZING NUCLEIC ACID POLYMERS AND RELATED COMPONENTS

RELATED APPLICATIONS

This application is a continuation of U.S. patent application Ser. No. 11/181,695, filed Jul. 14, 2005 and claims priority under 35 U.S.C. 119(e) to U.S. Provisional Patent Application Ser. No. 60/587,997, filed Jul. 14, 2004, the entire contents of which are hereby incorporated by reference in their entirety.

FIELD OF THE INVENTION

The invention relates generally to nucleic acid polymer identification, sequencing and/or detection, and more specifically to systems and methods of identifying, sequencing and/ or detecting, nucleic acid polymer using a particle (e.g., electron) beam, as well as related components.

BACKGROUND OF THE INVENTION

There are a variety of methods for sequencing nucleic acid molecules. Historically, common methods have been based on chemical (e.g., Maxam and Gilbert sequencing) or enzymatic (e.g., Sanger dideoxy sequencing and exonuclease-based sequencing) reactions that create specific truncated nucleic acid molecules that are then separated by electrophoretic techniques in order to determine their relative length. More recently, potentially higher throughput techniques have been developed including pyro-sequencing and hybridization-based sequencing methods. Even with improvements in such methods, however, the cost and speed of nucleic acid sequencing should be improved to facilitate widespread genome sequencing (useful in molecular medicine and pharmacogenomics, for example) and other uses of nucleic acid sequencing.

U.S. Patent Application Publication Nos. 2002/0086317 and 2004/0038261 (Nagayama) disclose a DNA sequencer system that uses base-specific heavy-atom labeling for imaging via electron microscopy. The Nagayama technique uses a single-stranded DNA that relies on Watson-Crick bonding between the nucleic acid being sequenced and labeled bases. Also, the Nagayama bases are not nucleotides, but, rather are bases without the polymerizable units from which a nucleic acid molecule can be made. This results in heavy-atom labels being held to the intended bases relatively weakly. Thus, in Nagayama's method, the labeled bases are susceptible to displacement from the original single strand by the electron beam being used for imaging, which reduces or eliminates meaningful data applicable to sequencing efforts.

Nagayama's technique also may be limited in its ability to archive nucleic acids in a manner other than as digital data. Nagayama's technique involves imaging only on the basis of relative signal intensity. Moreover, in the Nagayama technique, resolution may not be high enough to determine distances between heavy atoms of a label, or the pattern of arrangement that the heavy atoms have within the labeled base(s).

Thus there is a need for improved methods and systems that can determine nucleic acid sequences and amounts more quickly and effectively than presently available methods and systems.

SUMMARY OF THE INVENTION

The invention provides systems and methods of identifying, sequencing and/or detecting nucleic acid polymers, as well as related components (e.g., substrates, software and the like).

According to one aspect of the invention, methods of determining the sequence of a nucleic acid polymer are provided. The methods include forming a complementary strand of the nucleic acid polymer and identifying a sequence of nucleotides in the nucleic acid polymer and/or in the complementary strand using a particle beam.

In certain embodiments, the nucleic acid polymer and/or the complementary strand is DNA or RNA. In other embodiments, the nucleic acid polymer and/or its complementary strand is formed by a nucleic acid polymerase enzyme, such as using polymerase chain reaction (PCR).

In preferred embodiments, the nucleotides of the nucleic acid polymer and/or the complementary strand are modified to include labels. Preferably the labels are specific for each type of nucleotide. The labels can include one or more atoms, preferably three or fewer atoms, preferably a single atom. In some preferred embodiments, the atoms have an atomic number, alone or in aggregate, of greater than 55, while in other preferred embodiments the atoms have an atomic number, alone or in aggregate, of less than or equal to 55. In some embodiments, the atoms are halogen atoms.

Preferably nucleotide specific labels are incorporated in the nucleic acid polymer and/or the complementary strand during formation of the nucleic acid polymer and/or the complementary strand. In other embodiments, nucleotide specific labels are bonded to the nucleotides of the nucleic acid polymer and/or the complementary strand after formation of the nucleic acid polymer and/or the complementary strand.

In further embodiments, the nucleic acid polymer and/or the complementary strand are affixed to a substrate, and prior to the step of identification the nucleotides of the nucleic acid polymer and/or its complementary strand are substantially removed from the substrate, leaving the labels of the labeled nucleotides affixed to the substrate.

In still other embodiments, the step of identifying a sequence of nucleotides includes generating a particle beam, exposing the nucleic acid polymer and/or the complementary strand to the particle beam, and identifying the nucleotides due to characteristic changes to the particle beam. Preferably the nucleotides of the nucleic acid polymer and/or the complementary strand are modified to include labels, and more preferably the step of identifying the nucleotides includes detecting characteristic changes to the particle beam. In certain embodiments, the particle beam is a lepton beam; more preferably the lepton beam is an electron beam.

In other embodiments the nucleic acid polymer and/or the complementary strand are affixed to a substrate. The nucleic acid polymer and/or the complementary strand can be affixed to a substrate at one end of the nucleic acid polymer and/or the complementary strand, at both ends of the nucleic acid polymer and/or the complementary strand, and/or at a plurality of locations along the length of the nucleic acid polymer and/or the complementary strand.

In certain embodiments, the nucleic acid polymer and/or the complementary strand are substantially straightened prior to identifying the sequence. Preferably the nucleic acid polymer and/or the complementary strand are straightened by fluid flow, and more preferably the fluid flow includes molecular combing. The fluid can include one or more liquids, gases, phases or a combination thereof. In some embodiments, the nucleic acid polymer and/or the complementary strand are attached to a substrate and straightened by hybridization in the fluid flow to oligonucleotides that are attached to the substrate.

In additional embodiments, the step of identifying the nucleotides in the nucleic acid polymer and/or its complementary strand includes interpreting changes in the particle beam resulting from interactions with the nucleotides to detect the nucleotides in the nucleic acid polymer and/or its complementary strand, whereby the sequence of the nucleic acid polymer is determined. Preferably the nucleotides are labeled. The changes in the particle beam include changes in absorbance, reflection, deflection, energy or direction. The changes in the particle beam also can be changes in a spatial pattern, for example, a one dimensional pattern, a two dimensional pattern or a three dimensional pattern.

In further embodiments, the method also includes attaching the complementary strand and/or the nucleic acid polymer to a substrate. Preferably the attachment is by nucleic acid sequence-specific molecules, which preferably are oligonucleotides. In other preferred the substrate is derivatized to provide attachment points that are sequence non-specific. The complementary strand and optionally the nucleic acid polymer can be attached to the substrate in a grid pattern. Preferably the substrate includes a carbon thin film.

In other embodiments, the step of identifying the sequence of nucleotides includes performing a plurality of scans of the nucleic acid polymer and/or the complementary strand using the particle beam. Preferably at least 100 nucleotides are identified in each scan.

According to another aspect of the invention, methods of determining the sequence of a nucleic acid polymer are provided. The methods include synthesizing the nucleic acid polymer and/or its complementary strand using labeled ribonucleotide and/or deoxyribonucleotide triphosphates, and identifying labeled ribonucleotides and/or deoxyribonucleotides in the nucleic acid polymer and/or its complementary strand using a particle beam, wherein the labeled ribonucleotides and/or deoxyribonucleotides, when incorporated in the nucleic acid polymer and/or its complementary strand, are identifiable using the particle beam.

In certain embodiments, the nucleic acid polymer and/or the complementary strand is DNA or RNA. In other embodiments, the nucleic acid polymer and/or its complementary strand is synthesized by a nucleic acid polymerase enzyme, such as using polymerase chain reaction (PCR).

In preferred embodiments, the labels are specific for each type of nucleotide. The labels can include one or more atoms, preferably three or fewer atoms, preferably a single atom. In some preferred embodiments, the atoms have an atomic number, alone or in aggregate, of greater than 55, while in other preferred embodiments the atoms have an atomic number, alone or in aggregate, of less than or equal to 55. In some embodiments, the atoms are halogen atoms.

Preferably, the labels are incorporated in the ribonucleotide and/or deoxyribonucleotide triphosphates used in synthesis of the nucleic acid polymer and/or the complementary strand. In other embodiments, nucleotide specific labels are bonded to the nucleotides of the nucleic acid polymer and/or the complementary strand after incorporation of the ribonucleotide and/or deoxyribonucleotide triphosphates into the nucleic acid polymer and/or the complementary strand.

In further embodiments, the step of identifying the labeled ribonucleotides and/or deoxyribonucleotides includes generating a particle beam, exposing the nucleic acid polymer and the complementary strand to the particle beam, and identifying the ribonucleotides and/or deoxyribonucleotides due to characteristic changes to the particle beam. Preferably the step of detecting the ribonucleotides and/or deoxyribonucleotides includes detecting characteristic changes to the particle beam. In certain embodiments, the particle beam is a lepton beam; more preferably the lepton beam is an electron beam.

In other embodiments the nucleic acid polymer and/or the complementary strand are affixed to a substrate. In certain embodiments, prior to the step of identification the ribonucleotides and/or deoxyribonucleotides of the nucleic acid polymer and/or its complementary strand are substantially removed from the substrate, leaving the labels of the labeled ribonucleotides and/or deoxyribonucleotides affixed to the substrate. The nucleic acid polymer and/or the complementary strand can be affixed to a substrate at one end of the nucleic acid polymer and/or the complementary strand, at both ends of the nucleic acid polymer and/or the complementary strand, and/or at a plurality of locations along the length of the nucleic acid polymer and/or the complementary strand.

In certain embodiments, the nucleic acid polymer and/or the complementary strand are substantially straightened prior to identifying the labeled ribonucleotides and/or deoxyribonucleotides. Preferably the nucleic acid polymer and/or the complementary strand are straightened by fluid flow, and more preferably the fluid flow includes molecular combing. The fluid can include one or more liquids, gases, phases or a combination thereof. In some embodiments, the nucleic acid polymer and/or the complementary strand are attached to a substrate and straightened by hybridization in the fluid flow to oligonucleotides that are attached to the substrate.

In additional embodiments, the step of identifying the nucleotides in the nucleic acid polymer and/or its complementary strand includes interpreting changes in the particle beam resulting from interactions with the nucleotides to detect the ribonucleotides and/or deoxyribonucleotides in the nucleic acid polymer and/or its complementary strand, whereby the sequence of the nucleic acid polymer is determined. Preferably the nucleotides are labeled. The changes in the particle beam include changes in absorbance, reflection, deflection, energy or direction. The changes in the particle beam also can be changes in a spatial pattern, for example, a one dimensional pattern, a two dimensional pattern or a three dimensional pattern.

In further embodiments, the method also includes attaching the complementary strand and/or the nucleic acid polymer to a substrate. Preferably the attachment is by nucleic acid sequence-specific molecules, which preferably are oligonucleotides. In other preferred the substrate is derivatized to provide attachment points that are sequence non-specific. The complementary strand and optionally the nucleic acid polymer can be attached to the substrate in a grid pattern. Preferably the substrate includes a carbon thin film.

In other embodiments, the step of identifying the sequence of nucleotides includes performing a plurality of scans of the nucleic acid polymer and/or the complementary strand using the particle beam. Preferably at least 100 nucleotides are identified in each scan.

According to another aspect of the invention, methods of determining the sequence of a nucleic acid polymer are provided. The methods include synthesizing a complementary strand of the nucleic acid polymer using labeled ribonucleotide triphosphates or deoxyribonucleotide triphosphates, attaching the nucleic acid polymer and/or the complementary strand to a substrate, substantially straightening the nucleic acid polymer and/or the complementary strand using molecular combing, generating a particle beam, exposing the nucleic acid polymer and the complementary strand to the particle beam through the complementary strand on the substrate, and interpreting changes in the particle beam resulting from interactions with the nucleotides to detect the labeled nucleotides in the complementary strand, whereby the sequence of a nucleic acid polymer is determined.

According to another aspect of the invention, methods of detecting the presence and/or identifying a nucleic acid polymer are provided. The methods include forming a complementary strand of the nucleic acid polymer, attaching the complementary strand and, optionally, the nucleic acid polymer to a substrate, and detecting the presence and/or identifying the complementary strand and/or the nucleic acid polymer using a particle beam.

In some embodiments, the step of identifying includes measuring the length or determining at least a partial sequence of the complementary strand and/or the nucleic acid polymer.

In certain embodiments, the nucleic acid polymer and/or its complementary strand is DNA or RNA. In other embodiments, the nucleic acid polymer and/or its complementary strand is formed by a nucleic acid polymerase enzyme, e.g., using polymerase chain reaction (PCR); preferably the nucleic acid polymerase enzyme is a DNA-dependent DNA polymerase, a RNA-dependent DNA polymerase or a RNA-dependent RNA polymerase.

In other embodiments, the nucleotides of the nucleic acid polymer and/or the complementary strand are modified to include labels. In preferred embodiments, the labels are specific for each type of nucleotide. The labels can include one or more atoms, preferably three or fewer atoms, preferably a single atom. In some preferred embodiments, the atoms have an atomic number, alone or in aggregate, of greater than 55, while in other preferred embodiments the atoms have an atomic number, alone or in aggregate, of less than or equal to 55. In some embodiments, the atoms are halogen atoms.

Preferably nucleotide specific labels are incorporated in the nucleic acid polymer and/or the complementary strand during formation of the nucleic acid polymer and/or the complementary strand. In other embodiments, nucleotide specific labels are bonded to the nucleotides of the nucleic acid polymer and/or the complementary strand after formation of the nucleic acid polymer and/or the complementary strand.

In further embodiments, the step of detecting the presence and/or identifying of the complementary strand and/or the nucleic acid polymer using a particle beam includes generating a particle beam, exposing the nucleic acid polymer and/or the complementary strand to the particle beam, and detecting the nucleotides of the complementary strand and/or the nucleic acid polymer due to characteristic changes to the particle beam.

In some embodiments, the nucleotides of the nucleic acid polymer and/or the complementary strand are modified to include labels. Preferably the step of detecting the ribonucleotides and/or deoxyribonucleotides includes detecting characteristic changes to the particle beam. In certain embodiments, the particle beam is a lepton beam; more preferably the lepton beam is an electron beam.

In certain embodiments, the nucleic acid polymer and/or the complementary strand are substantially straightened prior to identifying the sequence. Preferably the nucleic acid polymer and/or the complementary strand are straightened by fluid flow, and more preferably the fluid flow includes molecular combing. The fluid can include one or more liquids, gases, phases or a combination thereof. In some embodiments, the nucleic acid polymer and/or the complementary strand are attached to a substrate and straightened by hybridization in the fluid flow to oligonucleotides that are attached to the substrate.

In additional embodiments, the step of identifying the nucleotides in the nucleic acid polymer and/or its complementary strand includes interpreting changes in the particle beam resulting from interactions with the nucleotides to detect the nucleotides in the nucleic acid polymer and/or its complementary strand, whereby the presence of the nucleic acid polymer is determined and/or the nucleic acid polymer is identified. Preferably the nucleotides are labeled. The changes in the particle beam include changes in absorbance, reflection, deflection, energy or direction. The changes in the particle beam also can be changes in a spatial pattern, for example, a one dimensional pattern, a two dimensional pattern or a three dimensional pattern.

In further embodiments, the method also includes attaching the complementary strand and/or the nucleic acid polymer to a substrate. Preferably the attachment is by nucleic acid sequence-specific molecules, which preferably are oligonucleotides. In other preferred the substrate is derivatized to provide attachment points that are sequence non-specific. The complementary strand and optionally the nucleic acid polymer can be attached to the substrate in a grid pattern. Preferably the substrate includes a carbon thin film.

In other embodiments, the method also includes quantifying the amount of the complementary strand and/or the nucleic acid polymer.

According to another aspect of the invention, a device is provided that includes a substrate that is substantially transparent to a particle beam, and nucleic acid polymer binding sites on a surface of the substrate.

In some embodiments the substrate is substantially transparent to an electron beam. Preferably the substrate includes a carbon thin film.

In other embodiments, the device also includes a support that is substantially transparent to a particle beam.

Preferably the substrate is less than 5 nm thick, more preferably less than 2 nm thick, still more preferably less than 1.5 nm thick, and yet more preferably less than 1.1 nm thick.

In other embodiments, the nucleic acid polymer binding sites are formed at predetermined positions on the surface of the substrate, preferably in a grid pattern. In certain embodiments, the nucleic acid polymer binding sites are sequence specific, preferably oligonucleotides. In other embodiments, the nucleic acid polymer binding sites are not sequence specific.

In further embodiments, the device also includes one or more nucleic acid polymers affixed to the nucleic acid polymer binding sites. Preferably the one or more nucleic acid polymers are modified to include labels.

According to another aspect of the invention, methods for making a device are provided. The methods include obtaining a substrate that is substantially transparent to a particle beam, and forming nucleic acid polymer binding sites on a surface of the substrate.

In some embodiments the substrate is substantially transparent to an electron beam. Preferably the substrate includes a carbon thin film. In some embodiments, the nucleic acid polymer binding sites are formed at predetermined positions on the surface of the substrate, preferably in a grid pattern.

In other embodiments, the method also includes attaching to the substrate a support that is substantially transparent to a particle beam.

Preferably the substrate is less than 5 nm thick, more preferably less than 2 nm thick, still more preferably less than 1.5 nm thick, and yet more preferably less than 1.1 nm thick.

In certain embodiments, the nucleic acid polymer binding sites are sequence specific, preferably oligonucleotides. In other embodiments, the nucleic acid polymer binding sites are not sequence specific.

In still other embodiments, the methods also include affixing one or more nucleic acid polymers to the nucleic acid polymer binding sites. Preferably, the one or more nucleic acid polymers are modified to include labels.

According to another aspect of the invention, systems designed to detect the presence of, determine the sequence of and/or identify a nucleic acid polymer are provided. The systems include: a sample chamber; a particle beam generator associated with the chamber; a sample comprising a labeled complementary strand of a nucleic acid polymer, wherein the sample, when positioned in the chamber, is exposed to a particle beam generated by the particle beam generator resulting in an interaction between the particle beam and the complementary strand; and a detector constructed and arranged to collect particle beam species after the interaction.

In some embodiments, the system also includes a data analysis module operative to receive and analyze signals from the detector. Preferably the data analysis module is operative to analyze signals related to absorbance, reflection, deflection, energy or direction. In other embodiments, the data analysis module is operative to analyze pattern recognition techniques to analyze the signals.

In further embodiments, the system also includes a user interface operative to control a display of information received and/or generated by the data analysis module.

In preferred embodiments, the particle beam generator is an electron beam generator.

The system in other embodiments also includes a feedback module designed to calibrate the system based on nucleic acid polymer data.

According to another aspect of the invention, systems designed to detect the presence of, determine the sequence of and/or identify a nucleic acid polymer are provided. The systems include: a sample chamber; a particle beam generator associated with the chamber; a detector constructed and arranged to collect particle beam species after interaction between the particle beam and a sample comprising the nucleic acid polymer and/or a complementary strand of the nucleic acid polymer; a data analysis module designed to analyze signals related to the particle beam species to determine information related to the nucleic acid polymer; and a feedback module designed to calibrate the system based on the information.

In some embodiments, the sample includes a labeled complementary strand of a nucleic acid polymer.

In certain embodiments, the feedback module is designed to calibrate the system based on a base-base distance of the nucleic acid polymer. In other embodiments, the feedback module is designed to calibrate the system based on known geometries of the nucleic acid polymer.

Also provided in accordance with another aspect of the invention are methods for calibrating a particle beam instrument. The methods include acquiring data related to a nucleic acid polymer; and calibrating the instrument based on the data. Preferably the data is related to a base-base distance of the nucleic acid polymer. In some embodiments, the calibrating includes calibrating the instrument based on known geometries of the nucleic acid polymer.

According to another aspect of the invention, systems are provided for detecting, sequencing and/or identifying a nucleic acid polymer based on particle beam species detected by a detector, the particle beam species resulting from exposure of a sample comprising a nucleic acid polymer and/or its complementary strand to a particle beam. The systems include a data analysis module operative to receive one or more signals from the detector, the one or more signals representing the particle beam species, and to detect, sequence and/or identify the nucleic acid polymer and/or its complementary strand comprised in the sample based at least in part on the received one or more signals. Preferably the nucleic acid polymer and/or its complementary strand is labeled.

In some embodiments, the particle beam species has one or more of the following properties: absorbance, reflection, deflection, energy and direction, and the data analysis module is operative to analyze the one or more signals to determine values of the one or more properties.

In other embodiments, the data analysis module is operative to access a data resource comprising nucleic acid polymer information, the data resource including a data structure having a plurality of entries, each entry specifying information about a respective nucleic acid polymer sequence. Preferably the data analysis module is operative to partially sequence the nucleic acid polymer based on the one or more signals, the data analysis module further comprising: a combining module to combine the partial sequence with sequencing information of the nucleic acid polymer accessed from the data resource. In preferred embodiments the data analysis module includes a comparison module operative to compare information determined from the one or more signals to the information specified by one or more of the data structure entries. Preferably the comparison module is operative to use pattern recognition techniques to compare the information determined from the one or more signals to the information specified by the one or more the data structure entries.

In other embodiments the data analysis module includes a user interface module to display information received and/or generated by the data analysis module to a user.

In further embodiments the particle beam to which the sample is exposed is generated by a particle beam generator, and the data analysis module includes a feedback module operative to provide one or more feedback signals to the particle beam generator and/or the detector, the one or more feedback signals specifying information determined at least in part from the one or more signals received from the detector. Preferably the one or more feedback signals include information for calibrating the particle beam generator. In preferred embodiments the feedback module is operative to generate the one or more feedback signals based at least in part on known geometries of the nucleic acid polymer. The data analysis module preferably includes a storage module operative to store information received and/or generated by the data analysis module on a computer-readable medium.

In some embodiments the sample includes a plurality of molecules of a same nucleic acid polymer and/or its complementary strand, and a plurality of particle beam species results from exposure of the plurality of molecules of the sample to the particle beam, the one or more signals representing the plurality of particle beam species, wherein the data analysis module is operative to partially sequence the nucleic acid polymer based on a first of the plurality of molecules to produce a first partial sequence, and to partially sequence the nucleic acid polymer based on a second of the plurality of molecules to produce a second partial sequence, and wherein the data processing module further includes a combining module to combine the first and second partial sequences.

According to another aspect of the invention, a computer-readable medium is provided having computer-readable signals stored thereon that define instructions that, as a result of being executed by a computer, control the computer to perform a process of detecting, sequencing and/or identifying a nucleic acid polymer based on particle beam species detected by a detector, the particle beam species resulting from exposure of a sample comprising a nucleic acid polymer and/or its complementary strand to a particle beam. The process includes: receiving one or more signals from the detector, the one or more signals representing the particle beam species; and detecting, sequencing and/or identifying the nucleic acid polymer and/or its complementary strand comprised in the sample based at least in part on the received one or more signals. Preferably the nucleic acid polymer and/or its complementary strand is labeled.

In some embodiments, the particle beam species has one or more of the following properties: absorbance, reflection, deflection, energy and direction, and the act of detecting, sequencing and/or identifying includes analyzing the one or more signals to determine values of the one or more properties.

In other embodiments, the act of detecting, sequencing and/or identifying includes accessing a data resource comprising nucleic acid polymer information, the data resource including a data structure having a plurality of entries, each entry specifying information about a respective nucleic acid polymer sequence. Preferably the act of detecting, sequencing and/or identifying includes partially sequencing the nucleic acid polymer based on the one or more signals to produce a partial sequence; accessing partial sequence information of the nucleic acid polymer from the data resource; and combining the partial sequence with the partial sequence information. In preferred embodiments the act of detecting, sequencing and/or identifying includes comparing information determined from the one or more signals to the information specified by one or more of the entries. In some of these embodiments, the act of detecting, sequencing and/or identifying preferably includes using pattern recognition techniques to compare the information determined from the one or more signals to the information specified by the one or more entries.

In further embodiments, the process further includes displaying information determined from the one or more received signals to a user.

In other embodiments the particle beam to which the sample is exposed is generated by a particle beam generator, and the process further includes providing one or more feedback signals to the particle beam generator and/or the detector, the one or more feedback signals specifying information determined at least in part from the one or more signals received from the detector. Preferably the act of providing includes providing one or more feedback signals that include information for calibrating the particle beam generator. In some embodiments the process further includes generating the one or more feedback signals based at least in part on known geometries of the nucleic acid polymer.

In other embodiments the process further includes storing information determine from the one or more signals on a computer-readable medium.

In further embodiments the sample includes a plurality of molecules of a same nucleic acid polymer and/or its complementary strand, and a plurality of particle beam species result from exposure of the plurality of molecules of the sample to the particle beam, the one or more signals representing the plurality of particle beam species, and the act of detecting, sequencing and/or identifying includes partially sequencing the nucleic acid polymer based on a first of the plurality of molecules to produce a first partial sequence; partially sequencing the nucleic acid polymer based on a second of the plurality of molecules to produce a second partial sequence; combining the first and second partial sequences.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures may be represented by a single numeral or notation (though not always). For purposes of clarity, not every component is labeled in every figure. Nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Systems and methods of sequencing, identifying and/or detecting nucleic acid polymers, such as DNA, are provided.

The methods can involve using a particle beam, such as an electron beam, to obtain information regarding the nucleic acid polymer. For example, a sample of DNA can be exposed to a particle beam and changes in the beam resulting from interaction with the sample may form a pattern which can be interpreted to provide the information. In some embodiments, a particle beam instrument (e.g., an electron microscope) can be used to directly view samples of DNA. The samples may be labeled (e.g., using atoms or molecules attached to a strand of DNA) to facilitate detection and identification of nucleotides of the sample. As described further below, the methods can enable nucleic acid sequencing, identifying and/or detection at high speeds, low costs, and high accuracy, amongst other advantages.

Figure 1:
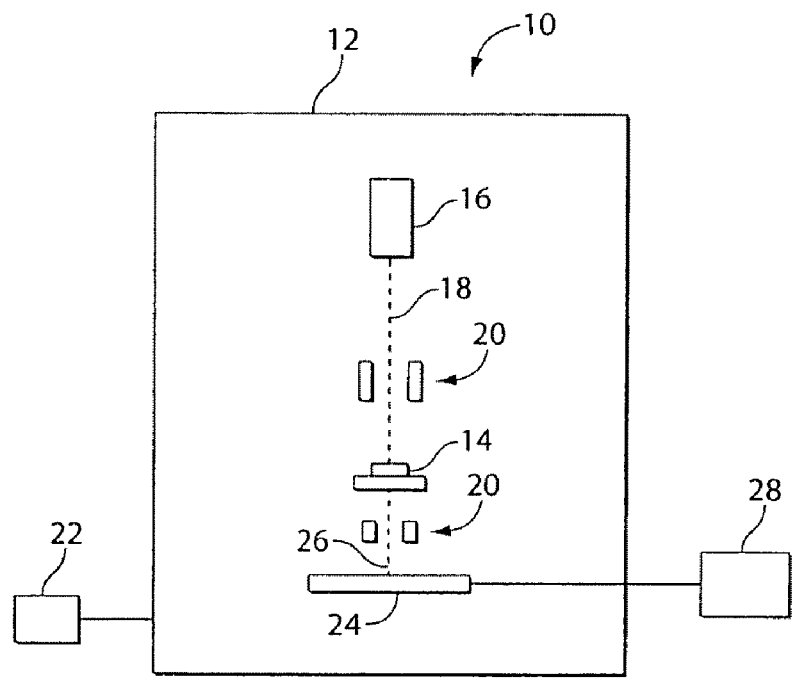
FIG. 1 is a nucleic acid polymer identification, sequencing and/or detection system according to one embodiment of the invention.

FIG. 1 shows a system 10 for identifying, sequencing and/or detecting nucleic acid polymers according to one embodiment of the invention. The system includes a chamber 12 in which a sample 14 is positioned. In this embodiment, a vacuum pump 22 is associated with the chamber to maintain sufficiently low vacuum (e.g., less than about $10^{-5}$ torr) during use. A particle beam generator 16 is designed to generate a particle beam 18. As shown, one or more lens arrangements 20 (which may include a single lens or multiple lenses) is used to direct and/or focus the particle beam on the sample. A detector 24 is positioned in the chamber to collect particle beam species 26 after the interaction between the particle beam and the sample. One or more lens arrangements 20 can be positioned between the sample or substrate and the detector 24 to expand the particle beam species 26 onto the detector 24. As shown, the detector may be positioned beneath the sample to collect beam species transmitted through the sample. The detector transmits electrical signals representative of the collected beam species to a data analysis module 28. As described further below, the data analysis module may be configured to interpret the data (e.g., for detecting, sequencing and/or identifying nucleic acids) and/or compare it to a known library of data patterns in order to detect, sequence and/or identify the nucleic acid polymer.

It should be understood that systems of the invention may have a variety of configurations different than that shown in the embodiment of FIG. 1.

In general, sample 14 is in a suitable form that may be analyzed to determine the sequence and/or presence of a nucleic acid polymer. In certain embodiments, it is preferred that the sample be formed of one or more complementary strands of the nucleic acid polymer. In other embodiments, the sample may be formed of one or more strands of the nucleic acid polymer along with or separate from the complementary strand.

Figure 2:
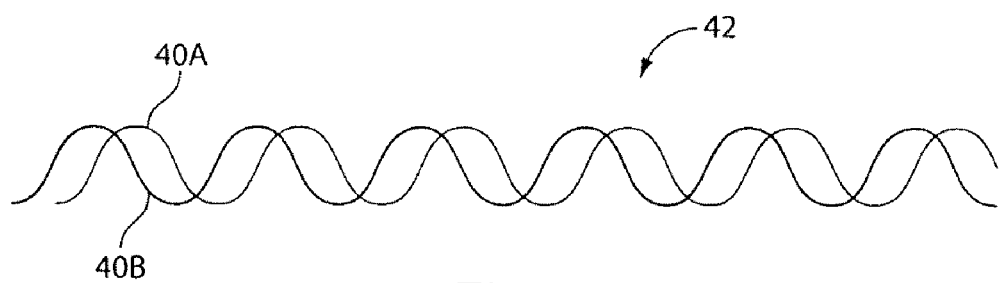
FIG. 2 shows a double stranded portion of a nucleic acid molecule.
Figure 3:
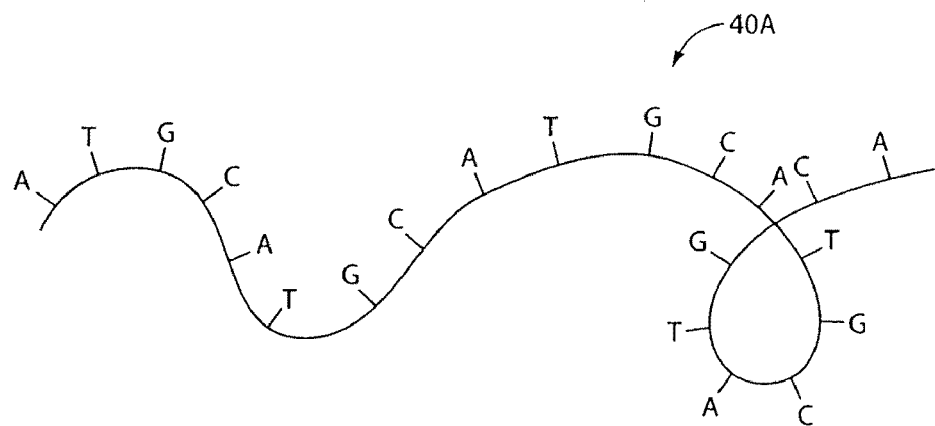
FIG. 3 shows a single stranded portion of the nucleic acid molecule (SEQ ID NO:4), with detail showing unpaired nucleotides.

Conventional techniques may be used to form a complementary strand of a nucleic acid polymer and/or the polymer itself. Typically, the first step in forming the complementary strand is to obtain a single strand of a nucleic acid polymer. Any suitable technique may be used to obtain a single strand. In some embodiments, a single strand may be obtained by separating a first strand 40A from a second strand 40B in a double-stranded structure 42 as shown in FIG. 2. Standard denaturing processes (e.g., thermal, enzymatic) which break the hydrogen bonding between the strands may be used. In other embodiments, a single strand can be created by synthesizing it from a template. For example, polymerase chain reaction (PCR) or reverse transcriptase processes that are well known in the art may be used. In other embodiments, a single strand may be chemically synthesized one nucleotide at a time, for example, in an oligonucleotide synthesis process. Such synthetic processes are well known in the art and can be automated. It is also possible to obtain a single strand by purifying it from a natural source, such as single stranded RNA from cells. Combinations of the foregoing (and other methods known to those of skill in the art) also can be used. FIG. 3 shows strand 40A, after separation, including nucleic acids.

Figure 4:
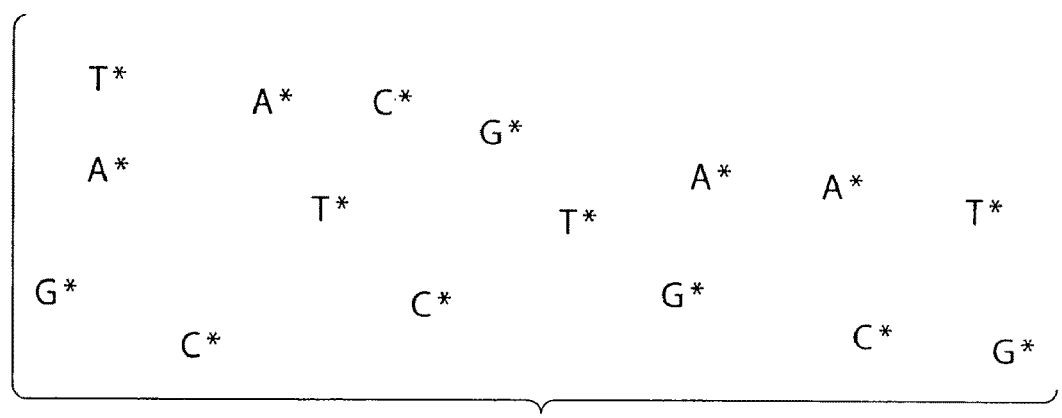
FIG. 4 shows a randomly ordered mixture of labeled dNTP's prior to polymerization onto the single strand.
Figure 5:
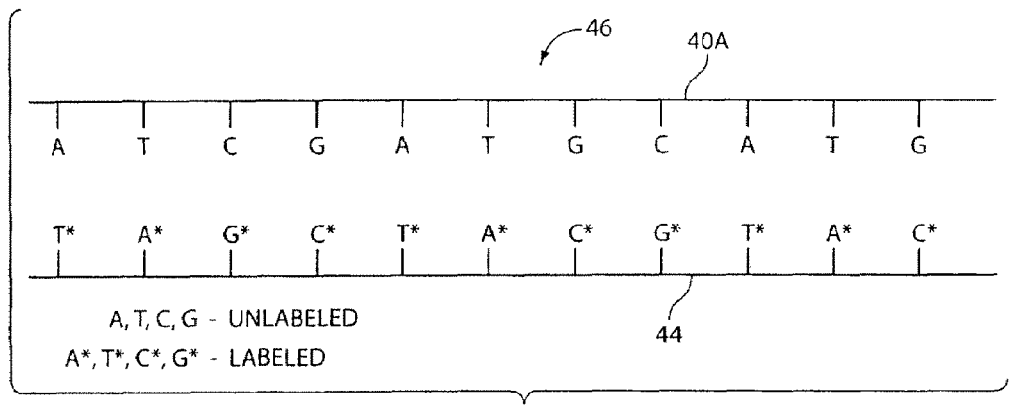
FIG. 5 shows the original single-stranded nucleic acid molecule (upper strand, SEQ ID NO:5) and labeled complementary strand (lower strand, SEQ ID NO:6) after polymerization (for clarity, shown without the helix conformation that would result).

A complementary strand of a nucleic acid polymer can be created from the single strand using any suitable conventional technique. For example, standard polymerization techniques may be used including polymerase chain reaction (PCR) (e.g., standard PCR, long PCR protocols). The techniques generally involve exposing the single strand to an excess of nucleotides under the proper reaction conditions. The nucleotides may be labeled, as described in further below, and shown schematically in FIG. 4. In some embodiments, single or multiple polymerase enzymes are used to facilitate reactions. Polymerase enzymes include DNA-dependent DNA polymerases (including thermostable enzymes such as Taq polymerase), RNA-dependent DNA polymerases (e.g., reverse transcriptases) and RNA-dependent RNA polymerases. In other embodiments, enzymes need not be used (e.g., in vitro chemical synthesis). Other suitable components (e.g., nucleotide primers, other enzymes such as primases, and the like) may also be present. FIG. 5 shows a structure 46 including complementary strand 44 which includes is labeled, as described further below, bonded to first strand 40A.

It should be understood that structure 46 may differ from structure 42 in FIG. 2 in that complementary strand 44 may be modified to include other components that would not otherwise be present in a DNA strand. For example, the complementary strand may be modified to include labels (e.g., during or after formation) that facilitate detection and identification of nucleotides in methods of the invention. Labels (e.g., atoms or molecules) when exposed to a particle beam create characteristic particle beam species that may be detected and identified using the systems and methods of the invention. In the illustrative embodiment, the labeled nucleotides are indicated by an asterisk (e.g., A*, T*, C*, G*). Similarly, the nucleic acid polymer also can be modified to include labels. This advantageously is done during synthesis of the nucleic acid, for example using PCR, which typically results in the synthesis of both strands (i.e., the nucleic acid polymer and its complementary strand). However, in certain embodiments of the invention labels are not utilized.

Figure 6:
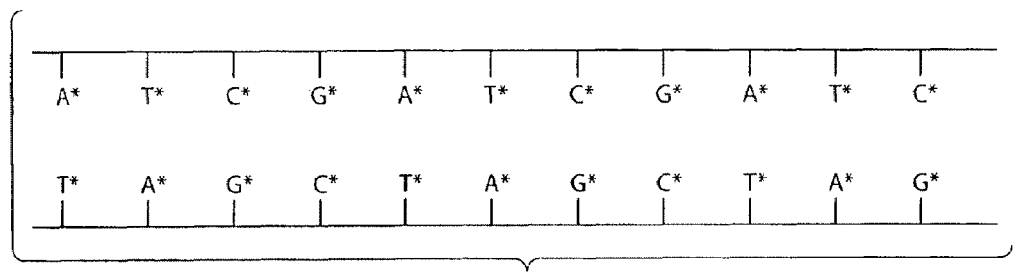
FIG. 6 shows a double strand (upper strand, SEQ ID NO:7; lower strand, SEQ ID NO:8) that has resulted from polymerizing labeled dNTP's onto a strand that already has labels (for clarity, shown without the helix conformation that would result).

When labels are present, it may be preferable to attach the labels to nucleotides of the complementary strand only (e.g., as shown in FIG. 5) or to both strands of the nucleic acid (e.g., using a post-synthesis chemical labeling step) or to incorporate the labels in the complementary strand only (e.g., using a single round of PCR) or to both strands of the nucleic acid (e.g., using two or more rounds of PCR and as shown in FIG. 6). In certain embodiments, specific types of label are respectively attached to each type of nucleotide (e.g., cytosine triphosphate (CTP), adenosine triphosphate (ATP), thymine triphosphate (TTP), uracil triphosphate (UTP), guanosine triphosphate (GTP); conventionally these nucleotides as incorporated into nucleic acid molecules are referred to by a single letter, e.g., A, C, G, T or U). For example, for labeling DNA, a first type of label is attached to a first nucleotide type (e.g., CTP); a second type of label is attached to a second nucleotide type (e.g., ATP); a third type of label is attached to a third nucleotide type (e.g., TTP); and a fourth type of label is attached to a fourth nucleotide type (e.g., GTP). Thus, as described further below, nucleotide types may be identified by identifying a particular labels. Modified (non-natural) or atypical natural nucleotides also can be used, in which the bases, sugars or phosphate moieties can be different than those present in typical naturally occurring nucleotides (e.g., in A, C, G, T and U). One example of this is "locked" nucleic acids, which for example can be a bicyclic nucleic acid where a ribonucleoside is linked between the 2'-oxygen and the 4'-carbon atoms with a methylene unit. Mixtures of the foregoing can be employed in the invention.

It should be understood that, as used herein, a "nucleotide" comprises a nitrogenous base, a sugar molecule (e.g., deoxyribose in DNA, ribose in RNA) and one or more (typically 1-3) linking groups (e.g., phosphate, peptide). A typical nucleotide is a nucleotide triphosphate, such as cytosine triphosphate as referred to above. As used herein, a "nucleoside" comprises a nitrogenous base and a sugar molecule, as described above, but no linking group. As used herein, a "base" comprises a nitrogenous base, but not the sugar molecule or linking group. Because of these composition differences, a nucleotide can be polymerized into a nucleic acid polymer, but a nucleoside or base cannot. As described further below, one advantage of certain embodiments of the present invention is that labels may be attached to nucleotides, which may be polymerized into nucleic acid polymer, as opposed to nucleic acid bases. Note, however, that a "base pair" is conventionally used to denote pairs of nucleotides that are bound in a sequence specific manner, e.g., Watson-Crick pairing such as A-T and C-G, in a double stranded nucleic acid polymer. However, this term also can refer to pairings of nucleosides or bases, which by definition are not part of nucleic acid polymers.

One of the advantages of having each nucleotide type bearing a unique label is that only a single "data read" is needed to obtain the sequence directly. Some interpretation as to which strand a given nucleotide is on may be required. Labeling each type of nucleotide uniquely also allows for some flexibility in data interpretation, as each base pair is identified twice: each nucleotide is identified directly and there are two nucleotides per base pair, which provides an internal control for the correctness of the data read and sequence.

In other embodiments, each nucleotide type (e.g., C, A, T, U, G) in a given strand bears a unique label, but the labels on the other strand are different. This can be accomplished by using different sets of labeled nucleotides in sequential PCR cycles, or other synthetic methods, and allows for greater ease in tracking the strand to which a nucleotide belongs.

In certain embodiments, not all nucleotide types need to be labeled. For example, if three nucleotide types (e.g., C, A, T) are labeled and the fourth (e.g., G) is unlabeled, then each "unlabeled" type may readily be identified as the fourth nucleotide type (e.g., G). The position of the unlabeled nucleotides can be inferred from observation of the distances between labeled nucleotides, given the highly regular spacing of nucleotides in nucleic acid polymers. In other embodiments, only two of the nucleotide types may be labeled. For example, a first set of sequencing data may be generated with two nucleotide types labeled (e.g., C, A) and a second set of sequencing data may be generated with the other two nucleotide types labeled (e.g., T, G). Both data sets may be processed to provide information regarding the entire sequence.

Alternatively, by labeling only two nucleotides (e.g., A, C) on both strands of a nucleic acid polymer, the sequence of either strand can be inferred from the sequence of the other strand. For example, all labeled adenines in one strand of a double stranded nucleic acid polymer will be bound to thymines on the opposite strand in accordance with Watson-Crick nucleotide binding rules. Thus, observation of an adenine on one strand allows one to infer the existence of a thymine in the corresponding position of the other strand of a double stranded nucleic acid. The positions of other nucleotides can likewise be directly read or inferred from observing a double stranded nucleic acid that incorporates only two nucleotide-specific labels.

The labels may be attached to nucleotides in a variety of different locations. In some embodiments, labels are attached to the nucleotides on, or within, the nitrogenous base (e.g., adenine, guanine, thymine, cytosine, uracil). For example, in these embodiments, labels may be attached to carbon/nitrogen rings in the base or may replace carbon or nitrogen atoms in the base. In other embodiments, labels are attached to the nucleotides on, or within, the sugar molecule (e.g., ribose in RNA, or deoxyribose in DNA). In other embodiments, labels are attached on, or within, linking groups of the nucleotides. For example, the labels may be attached on, or within, a phosphate linking group. The labels may be attached to oxygen substitutes, such as sulfur (e.g., alpha substituted phosphates, αS) or may replace the phosphorous atom at certain sites.

In certain embodiments, the labels are attached to the nucleotides by covalent bonding. As described further below, covalent bonding provides strong attachment between labels and nucleotides which can enable labeled samples to withstand exposure to relatively high particle beam energies (e.g., greater than about 50 kV for electron beams, for example about 80-120 kV) that may be important to detection and/or identification of nucleic acids. In contrast, the techniques described by Nagayama involve attaching labels using Watson-Crick bonding which is generally significantly weaker than covalent bonding and, thus, may not be able to withstand such high electron beam energies.

In certain embodiments, it is preferable that the labels are attached to nucleotides prior to the nucleotides forming the complementary strand (and/or copies of the first strand of the nucleic acid polymer). In these embodiments, the labels may be selected from types, as described further below, that do not prevent polymerase reactions that form the complementary strand (and/or copies of the first strand of the nucleic acid polymer). Thus, in these cases, the complementary strand is labeled during its formation.

However, in other embodiments, it may be desired to attach labels to nucleotides after formation of the complementary strand (and/or copies of the first strand of the nucleic acid polymer). In these cases, the nucleotides may have been modified (prior to formation of the complementary strand and/or copies of the first strand of the nucleic acid polymer) to include a suitable attachment site which can be bound, preferably covalently, to a desired label type. After formation, the nucleic acid strand(s) may be exposed to the labels which attach to the sites.

Methods of the invention may use any suitable label. In general, the label should be selected from types that are more easily detectable and identifiable than nucleotides, themselves, using methods of the invention that utilize a particle beam. In some embodiments, the labels comprise a combination of atoms which may be the same type or may be different types which form a group (e.g., trifluoro methyl). It may be preferable, in some cases, for the labels to comprise three or less atoms and, in some cases, a single atom. Suitable atoms for labeling include, but are not limited to: Cl, Br, I, U, Os, Pb, Au, Ag, Fe, Pt, Eu, Pd, Co, Hg, Gd, Cd, Zn, Ac, W, Mo, Mn, Rb, Cs, Ra, Ba, and Sr. Halogen atoms may be preferred in certain cases. In some embodiments, though not all, the labels may have an atomic number (alone or in aggregate) of greater than 55 in methods of the invention. Although, in other embodiments, it may be preferable for the labels to have an atomic number of less than or equal to 55 (alone or in aggregate), e.g., 17-55.

In certain methods of the invention, the complementary strand is separated from first strand to form a single complementary strand as shown which is used as the sample. The complementary strand may be separated from the first strand using conventional denaturing techniques (e.g., thermal, enzymatic). After separation, the first strand may be discarded, or may be retained and otherwise used.

In some cases, separation and use of the complementary strand can simplify detection and/or identification in subsequent method steps. Although, in some embodiments, the complementary strand and the first strand are not separated, and the double-stranded structure is used as a sample in the detection and/or identification steps.

In certain embodiments, when the complementary strand is separated from the first strand, the complementary strand is used as a template to create another strand which may be labeled. This can create a double-stranded structure which includes two labeled strands (i.e., the complementary strand and the new strand created from the complementary strand) as shown in FIG. 6. In certain methods, this double-stranded structure is used as the sample in the detection and/or identification steps.

Methods of the invention may involve attaching a sample (e.g., complementary strand, complementary strand and first strand, complementary strand and new strand), or more than one sample, to a substrate. When more than one sample is attached, the sample may be the same (i.e., based on the same sequence) or different. In general, the substrate should be suitable for exposure to a particle beam. In embodiments in which particle beam species transmitted through the sample are detected, the substrate should permit sufficient transmission of the particle beam.

The substrate is generally thin to enable sufficient particle beam transmission therethrough. For example, the substrate may be less than 5 nanometers (nm); in some cases, less than 2 nm; or, even less than 1.5 or 1.1 nm. The substrate may be formed of a single layer or multiple layers. In certain cases, the layer(s) may be cross-linked. Conventional techniques can be used to form the substrates including vapor deposition and FIB milling, amongst others.

Suitable substrate materials are known to those of skill in the art and can include carbon (e.g., pure carbon, graphene, diamond), boron nitride (e.g., having a cubic structure), aluminum and certain polymeric resins (e.g., FORMVAR® (polyvinyl formal)). In other embodiments, the substrate is formed of an organic materials such as a lipid, natural protein or synthetic protein. The substrate material may be doped with chemicals, for example, to cross-link layers or to facilitate attachment of the sample as described further below.

Samples may be attached to the substrate by chemically bonding at least a portion of the sample to the substrate. Suitable techniques are known to those of skill in the art. For example, molecules present on the surface of the substrate (e.g., pre-existing as part of the substrate or following derivatization of the substrate) may be used to bind to the sample. The molecules may be nucleic acid sequence specific molecules (e.g., oligonucleotides). In other cases, the substrate surface may be derivatized to provide attachment points that are sequence non-specific. In other cases, electrical charge may be used to bind the sample to the substrate surface. The attachment points for the samples can be spaced apart in a predetermined pattern, such as a grid or microarray.

A portion, or portions, of a sample may be attached to the substrate. In some cases, both ends of the sample (e.g., complementary strand, complementary strand and first strand, complementary strand and new strand) may be attached; in other cases, only one end of the sample may be attached; in some cases, one or more non-end portions along the length of the sample may be attached. The attachment at the end(s) or along the length of the nucleic acid molecule(s) can be facilitated, if desired, by including in the nucleic acid during synthesis nucleotides capable of forming bonds with the substrate.

Figure 7:
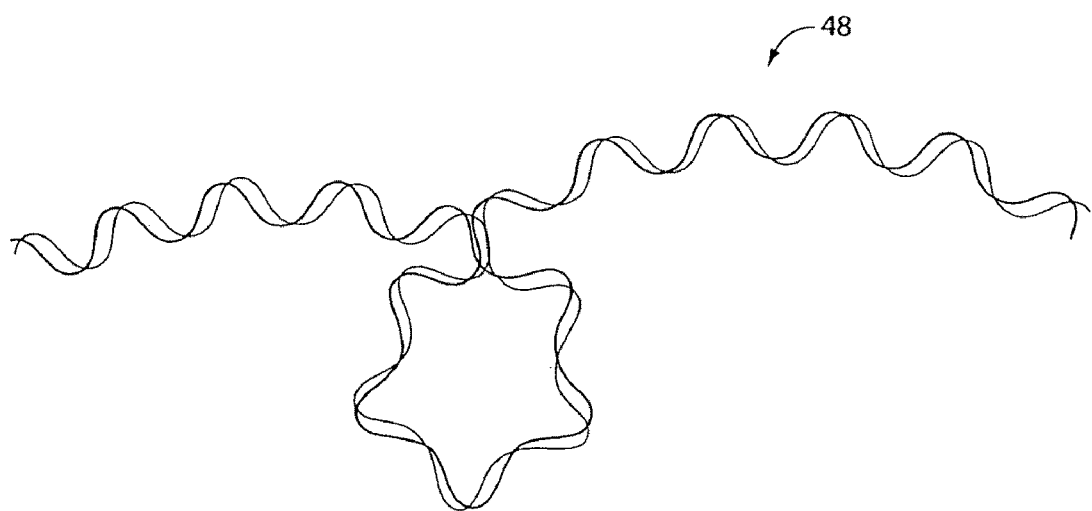
FIG. 7 shows the helix conformation that would result from labeled double strands, whether one or both strands are labeled. The possibility of looping and curving is shown.
Figure 8A:
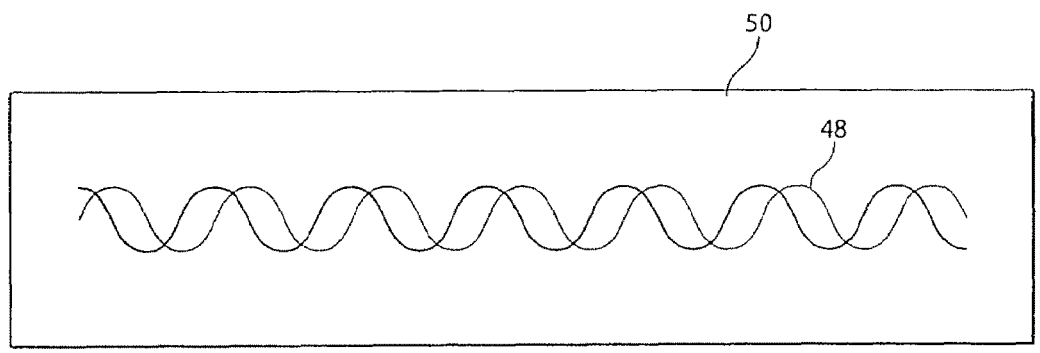
FIGS. 8A and 8B respectively show a top view and a cross-sectional view of a strand that has been substantially straightened and is attached to a substrate.
Figure 8B:
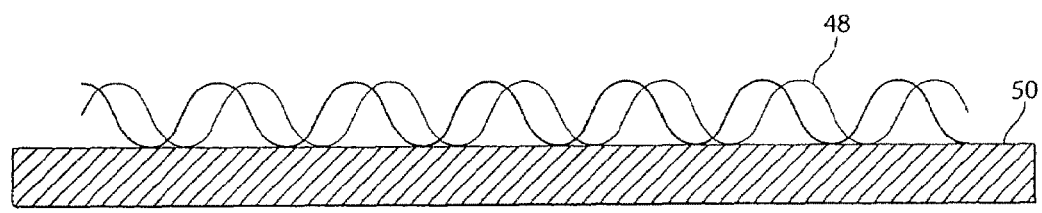

FIG. 7 illustrates a helical conformation of a labeled double strand 48 which, as shown, may be looped and curved. Certain methods of the invention involve substantially straightening a sample (e.g., labeled double strand) prior to, during, or even after, attachment to the substrate. This can facilitate detection and/or identification. FIGS. 8A and 8B show a labeled double strand 48 that has been substantially straightened and is attached to a substrate 50. The labeled double strand may be attached to the substrate, for example, via a linking bond to a bonding site as described further below. Conventional techniques may be used to straighten the sample. For example, a sample may be straightened using fluid flow (e.g., molecular combing). The fluid may comprise one or more liquids, gases, or combinations thereof. In certain embodiments, the sample is attached and straightened by hybridization in a fluid flow to oligonucleotides present on the substrate surface. In some cases, electrical fields may be used (either in the presence of fluid flow, or alone) to promote sample straightening. In embodiments in which more than one sample is attached to the substrate, it may be preferred for each sample to be aligned substantially parallel to one another to facilitate exposure to the beam. For example, "molecular combing" techniques may be used to align oligonucleotides on substrate surfaces. Suitable "molecular combing" techniques have been described, for example, in U.S. Pat. No. 6,303,296 or International Patent Publication No. WO 95/21939, which are incorporated herein by reference.

Figure 9A:
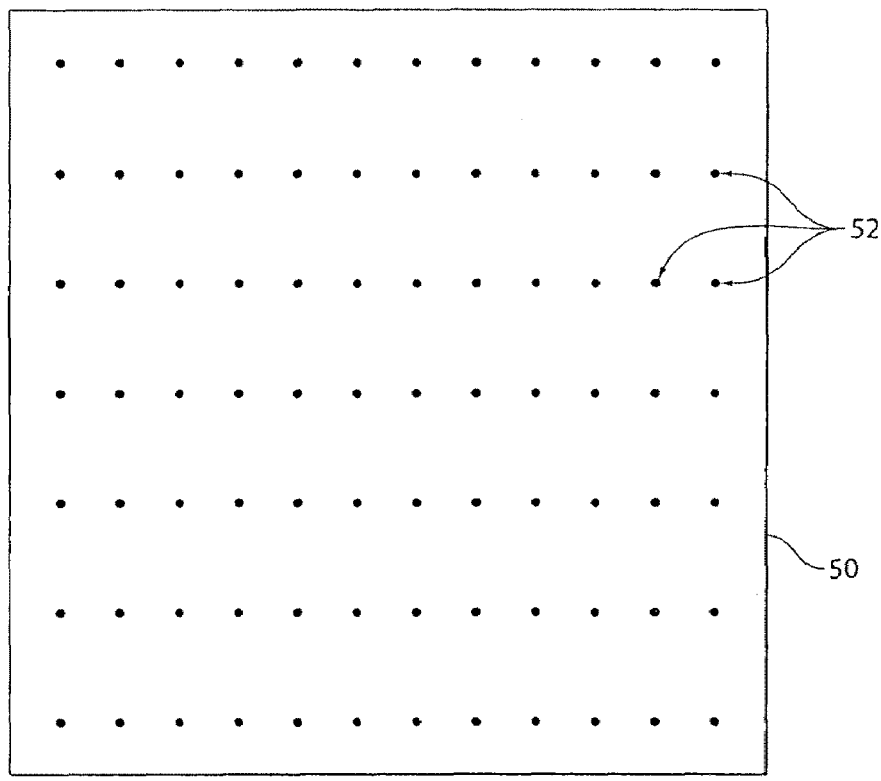
FIGS. 9A and 9B respectively show a top view and a cross-sectional view localized bonding sites arranged in a grid pattern on a substrate.
Figure 9B:
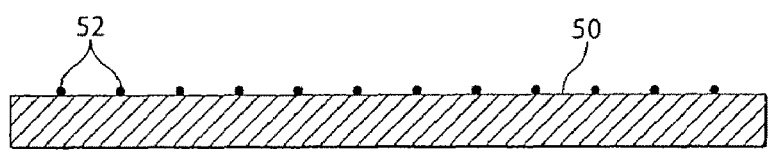

In certain embodiments, the surface of the substrate (or a majority of the substrate surface area) is homogenous. In these embodiments, substantially the entire surface of the substrate (or a majority of the substrate surface) is capable of bonding to a sample. In other embodiments, the substrate includes respective localized surface sites that are capable of bonding to a sample. For example, localized bonding sites 52 may be arranged in a grid pattern on substrate 50 as shown in FIGS. 9A and 9B.

The process of attaching the nucleic acid strand(s) to the substrate can be performed either with labels already included, partially included or not yet included. In the latter two cases, one or more types of labels are subsequently added to label the strand(s) on the substrate.

Following the attachment of the strand(s), excess solution(s) are removed. The substrate optionally can be washed to remove impurities.

In some methods, the nucleic acid material may be removed from the sample, while retaining the labels bonded to the substrate. For example, the nucleic acid material may be removed by dissolving, enzymatically digesting, evaporating (e.g., by reducing pressure and/or increasing temperature) or etching (e.g., by chemical or particle beam). When the nucleic acid is etched, a mask may be optionally used to protect the labels.

Figure 10:
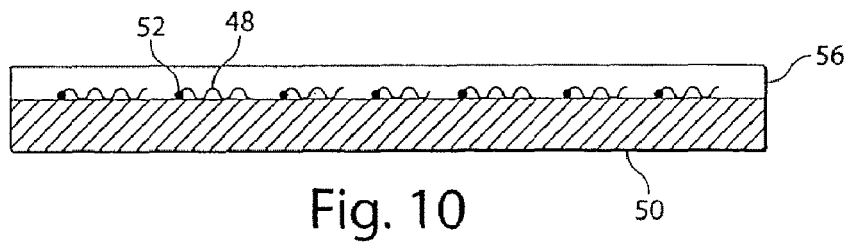
FIG. 10 shows such a protective layer formed over a sample on a substrate.

In certain embodiments of the invention, it may be preferred to further stabilize the sample(s) on the substrate. For example, a stabilizing layer of material may be provided over the sample(s). The stabilizing layer can be formed of any suitable material which should be sufficiently transparent to the particle beam. Suitable materials include the substrate materials described above. The stabilizing layer may be provided over the sample(s) by mechanically positioning or depositing (e.g., chemically or lithographically). FIG. 10 shows such a protective layer 56 formed over a sample (e.g., labeled double strand 48). The stabilizing layer may enable using high electron energies in subsequent processing steps which can be important for identifying, sequencing and/or detecting. The stabilizing layer also may provide a more stable material for archiving the nucleic acid molecules (or labels after removal of the nucleic acid molecules) for storage and/or subsequent analysis.

Methods of the invention involve exposing the sample to a particle beam. In certain embodiments, it is preferred that the particle beam is a lepton beam such as an electron beam. In other cases, the particle beam may be an x-ray beam. When an electron beam is used, beam generator 16 can be similar to those used in electron microscopy (e.g., transmission electron microscopy). Generator 16 produces a beam having a desired voltage which, for example, can be greater than 50 kV, e.g., 80-300 kV, preferably 80-120 kV. Beam energies are a function of both voltage and current. The beam current typically ranges between 5 to 25 μA, preferably between 8 and 15 μA. The specific beam energy depends, in part, on the specific analysis being performed.

Methods can include properly focusing the beam on the sample using a lens arrangement as known to those of skill in the art. Methods may also include a calibration step. In certain cases, the system may be automatically calibrated based on known information from nucleic acid molecules in the sample (such as known molecular geometries and structures) using a feedback loop. For example, data obtained from a nucleic acid sample using an electron beam may include internucleotide (e.g., interlabel) distances. As used herein, an internucleotide distance is the distance from one nucleotide base in one strand to the adjacent nucleotide base in the same strand. While the internucleotide distances of, for example, a DNA molecule are generally known, the internucleotide distance in any given sample may not correspond to the generally known distance, but will typically by substantially uniform within a sample as affixed to a substrate, particularly a sample that has been straightened, e.g., by treatment using molecular combing or like methods. Thus, after obtaining a data read on a given sample, various aspects of the system can be calibrated or adjusted using a feedback control system. For example, knowing the internucleotide distances permits feedback relevant to focusing the particle beam and movement of the sample relative to the particle beam.

Though systems of the invention may include several components similar to that of a conventional transmission electron microscope (e.g., beam generator, lens, etc.), certain systems of the invention may be more simple than typical conventional TEMs. For example, in some embodiments, the systems are simplified by limiting the magnification range, accelerating voltages, probe diameter, beam current, and sample flexibility, amongst other features. Also, problems related to spherical aberration in conventional TEMs may be limited, or eliminated, by using a lens arrangement that is pre-set for typical operating conditions for the system.

Characteristics of the particle beam are changed when the beam interacts with the sample. For example, one or more of the following characteristics of the particle beam may change: energy, direction, absorbance, reflection and deflection. Such changes may result from interactions between the particle beam and labels attached to nucleotides as described above. Specific types of labels may produce specific or characteristic changes. Thus, a label (and, the specific nucleotide to which it is attached) may be identified by recognizing the specific or characteristic beam changes.

Detector 24 collects particle beam species 26 after the interaction between the particle beam and the sample. The detector typically collects beam species that have been transmitted through the sample, though also can collect beam species that are reflected and/or scattered. The detector may include a charge coupled device (CCD). The CCD may directly convert the beam species into digital information. Technologies other than CCD technology may be used to convert the beam species into digital information, and are intended to fall within the scope of the invention.

Typically, the beam is scanned across the sample, which may occur by movement of the beam relative to the sample, by movement of the sample relative to the beam, or both. Certain methods involve scanning the beam across the sample multiple times.

A feedback loop may be used to optimize performance. In addition to the feedback loop described above in relation to internucleotide distances, one can integrate sample information gathered from scanning the sample with an electron beam reading device for additional feedback loops.

A feedback loop can be used to follow the path of the molecule(s) on the substrate, which can be used to reduce the number of pixels in the CCD that need to be read to just those capturing data in vicinity of molecule(s) of interest, thereby increasing number of data reads per second for substantially faster data analysis. This type of feedback loop can also be used to determine need to re-sample or over-sample data and/or to determine when the analysis of a particular sample is finished and/or when the machine is ready to move to next sample/molecule(s).

A feedback loop may be used to optimize performance. In addition to the feedback loop described above in relation to internucleotide distances, one can integrate sample information gathered from scanning the sample with an electron beam reading device for additional feedback loops.

A feedback loop can be used to follow the path of the molecule(s) on the substrate, which can be used to reduce the number of pixels in the CCD that need to be read to just those capturing data in vicinity of molecule(s) of interest, thereby increasing the number of data reads per second for substantially faster data analysis. This type of feedback loop can also be used to determine a need to re-sample or over-sample data and/or to determine when the analysis of a particular sample is finished and/or when the machine is ready to move to next sample/molecule(s).

In some embodiments of the invention, a nucleic acid polymer may be detected, and/or sequenced and/or identified based on particle beam species detected by a detector (e.g., the detector described above). Particle beam species may result from exposure of a sample comprising a nucleic acid polymer and/or its complementary strand to a particle beam (e.g., a lepton beam such as an electron beam). The nucleic acid polymer and/or its complementary strand may be labeled using techniques described herein. Such a method may be implemented using the system 60, including data analysis module 71, which will now be described in relation to FIG. 11.

Figure 11:
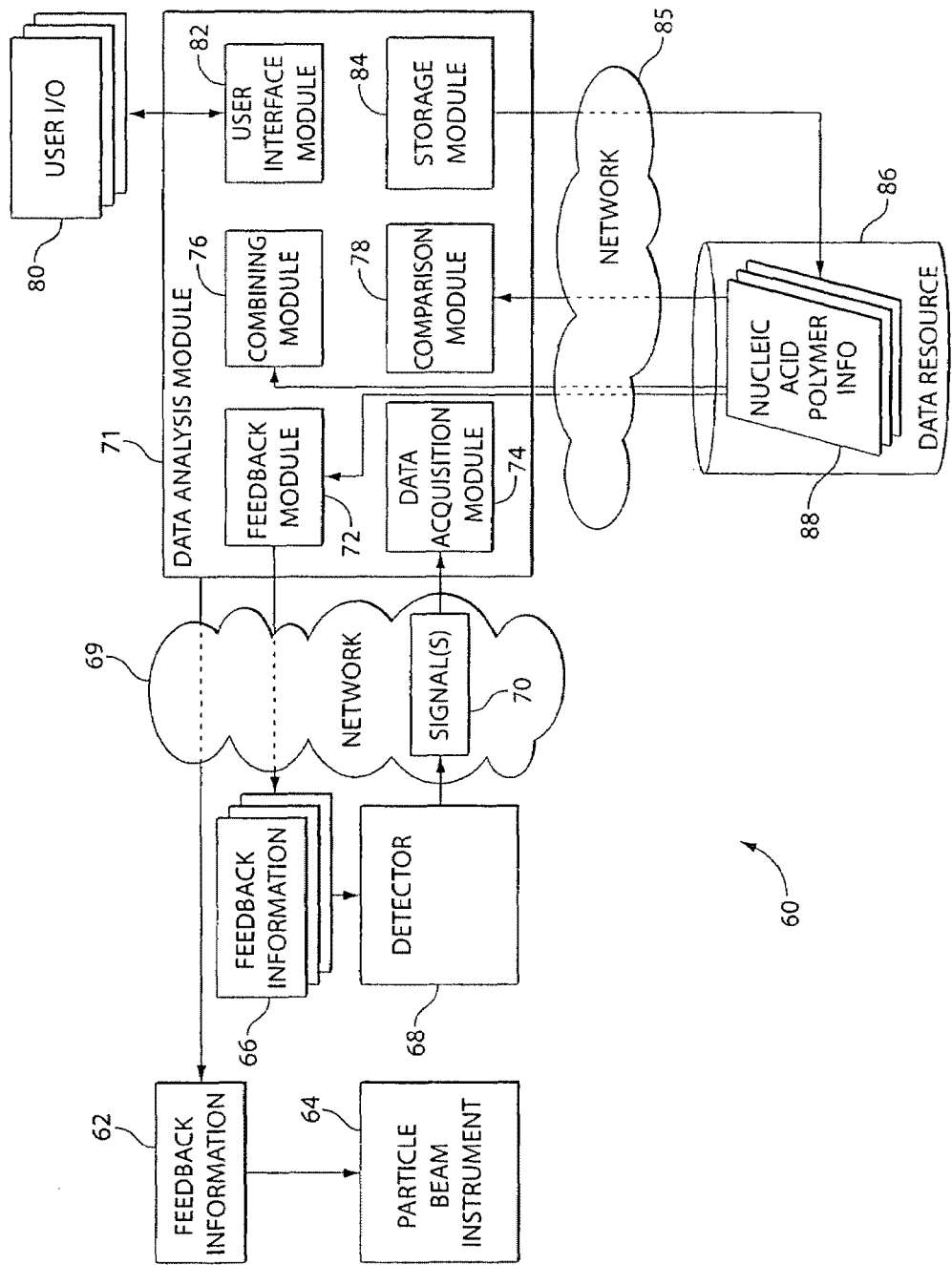
FIG. 11 is a block diagram illustrating an example of a system for detecting, and/or sequencing and/or identifying a nucleic acid polymer.

FIG. 11 is a block diagram illustrating an example of a system 60 for detecting, and/or sequencing and/or identifying a nucleic acid polymer based on particle beam species detected by a detector, the particle beam species resulting from exposure of a sample comprising a nucleic acid polymer and/or its complementary strand to a particle beam. System 60 is merely an illustrative embodiment of a system for detecting, and/or sequencing and/or identifying a nucleic acid polymer based on a particle beam species detected by a detector, and is not intended to limit the scope of the invention. Other implementation of such a system such as, for example, variations of system 60, are possible and are intended to fall within the scope of the invention.

The particle beam used to expose the sample may be generated by a particle beam generator, for example, as described above. Further, as described above, this particle beam may be a lepton beam such as, for example, an electron beam, and the nucleic acid polymer and/or its complementary strand may be labeled.

FIG. 11 is a block diagram illustrating an example of a system 60 for detecting, and/or sequencing and/or identifying a nucleic acid polymer based on particle beam species detected by a detector, the particle beam species resulting from exposure of a sample comprising a nucleic acid polymer and/or its complimentary strand to a particle beam. System 60 is merely an illustrative embodiment of a system for detecting, and/or sequencing and/or identifying a nucleic acid polymer based on a particle beam species detected by a detector, and is not intended to limit the scope of the invention. Other implementation of such a system such as, for example, variations of system 60, are possible and are intended to fall within the scope of the invention.

The particle beam used to expose the sample may be generated by a particle beam generator, for example, as described above. Further, as described above, this particle beam may be a lepton beam such as, for example, an electron beam, and the nucleic acid polymer and/or its complimentary strand may be labeled.

The data analysis module 71 may employ techniques similar to, or the same as, techniques employed by known machine vision systems (e.g., machines that can "see") such as, for example, systems available from Cognex Corporation of Natick, Mass.

System 60 may include any of: particle beam instrument 64; detector 68; software analysis module 71; network 69; network 85; data resource 86; other components; or any suitable combination of the foregoing. The particle beam instrument 64 and detector 68 may be of any type described herein.

Data analysis module 71 may be configured to receive one or more signals 70 from detector 68. The one or more signals may represent a particle beam species resulting from exposure of the sample comprising a nucleic acid polymer and/or its complementary strand. In some embodiments of the invention, data analysis module 71 and detector 68 reside on a same device, and the communication of the one or more signals 70 may be achieved through internal buses and other connections. In other embodiments, module 71 and detector 68 may be remotely located from each other on different devices, such that the one or more signals 70 may be transmitted across a network 69.

Data analysis module 71 may include a data acquisition module 74 to receive the one or more signals 70. The data acquisition module may be configured to amplify the one or more received signals and/or apply other known signal processing techniques. It should be appreciated that one or more of these signal processing techniques also may be employed by the detector 68.

Data analysis module 71 may be configured to detect and/or sequence and/or identify the nucleic acid polymer comprised in the sample based at least in part on the received one or more signals 70. For example, module 71 may be configured to perform different functions at different times. That is, it may be configured to detect a nucleic acid polymer for a given sample, and then configured differently to sequence a nucleic acid polymer for another (or the same) given sample, and configured differently yet again to identify another (or the same) given sample. Further, data analysis module 71 may be configured to perform different combinations of detecting, sequencing and/or identifying at different times. Configuring module 71 may be performed by: hard-coding software elements of module 71; setting values for configurable parameters manually or through software; electronically programming firmware elements of module 71; employing other known programming techniques or any suitable combination of the foregoing. Further, data analysis module 71 may be configured to identify one or more properties of a particle beam species represented by the one or more signals 70 and perform one or more of detecting, sequencing and identifying based on the identified property. That is, the operation of module 71 may be data-dependent.

The particle beam species represented by the one or more signals may have any of the following properties: absorbance; reflection, deflection; energy; direction; other properties; or any suitable combination of the foregoing. Data analysis module 71 may be configured to analyze the one or more received signals 70 to determine values of at least one (e.g., all) of the one or more properties. Further, as noted above, the data may be evaluated to determine the presence and absence of molecules (or atoms within molecules), number of molecules present, sequence of nucleotides or base pairs in nucleic acid molecules, lengths of nucleic acid molecules and shapes of nucleic acid molecules.

In some embodiments of the invention, data analysis module 71 is operative to access a data resource 86 comprising nucleic acid polymer information 88. One or more portions of the nucleic acid polymer information 88 and/or the data resource 86 may be disposed remotely from module 71, across network 85 on a separate device, as shown in FIG. 11. For example, at least a portion of the data resource may be the GenBank database, which is accessible via the Internet from the National Center for Biotechnology Information (NCBI), which is publicly accessible at the date of filing of this application at The website of the NCBI, ncbi.gov. Thus, one or more portions of information 88 may be accessed from the GenBank database. Further, one or more portions of information 88 and/or data resource 86 may reside on a same device as module 71.

Nucleic acid polymer information 88 may be arranged as and/or include a data structure including a plurality of entries, in which each entry specifies information about a respective nucleic acid polymer. For example, each entry may be an entry and/or record from the GenBank database.

Data analysis module 71 may be operative to compare information determined from the one or more signals 70 about the nucleic acid polymer and/or its complementary strand to one or more pieces of information accessed from information 88 of data resource 86. For example, module 71 may include a comparison module 78 configured to make such comparisons. In some embodiments of the invention, the comparison module 78 may be configured to use pattern recognition techniques to compare the information determined from the one or more signals to information specified by one or more entries of the nucleic acid polymer 88. For example, module 78 may be configured to compare information gleaned from the one or more signals to known data patterns corresponding to individual nucleotides having specific labels, individual base pairs of labeled nucleotides, distinct alleles, and distinct mutations (e.g., omission, repetition, inclusion of abnormal sequence, etc.). Computer module 78 may be configured using existing commercially-available or freely-available software for comparing patterns, and may be optimized for particular data comparisons that are conducted.

As noted above, in some embodiments of the invention, a feedback loop is employed to calibrate particle beam instrument 64, for example, based on known nucleic acid molecule geometries and the structures and complexes of nucleic acid molecules. For example, data analysis module 71 may include a feedback module 72 that provides feedback information 62 to particle beam instrument 64. Feedback module 72 also may be configured to provide feedback information 66 to detector 68 and/or other components of the systems described herein. Feedback information 62 may have been generated by one or more components of data module 71 and may have been determined based at least in part of the one or more signals 70 and/or one or more pieces of nucleic acid polymer information 88. For example, feedback information 62 may be generated using known geometries of the nucleic acid polymer obtained from nucleic acid polymer information 88.

In some embodiments of the invention, known information about a nucleic acid polymer (e.g., its molecular geometries) can be combined with information determined from the one or more signals 70 to detect, and/or sequence and/or identify a nucleic acid polymer included in the sample. For example, one or more components of data analysis module 71 may partially sequence a nucleic acid polymer of the sample based on the one or more signals 70. Further, other portions of the nucleic acid polymer sequence may be sequenced from nucleic acid polymer information 88 (e.g., from the GenBank database). The combining module 76 may be configured to combine (i.e., assemble) the partial sequence determined from the one or more signals 70 and the partial sequence determined from the nucleic acid polymer information 88, from which the nucleic acid polymer may be detected, and/or sequenced and/or identified. Using nucleic acid polymer information 88 to "fill in the gaps" in the partial sequence determined from the one or more signal 70 may be advantageous. For example, it may enable a reduced number of exposures of samples and resulting data reads (e.g., reception of one or more signals 70) necessary to detect, and/or sequence and/or identify a nucleic acid polymer within a sample.

In other embodiments of the invention, the data analysis module (e.g., through feedback information 62 from feedback module 72) may be configured to use information obtained about the presence, sequence and/or identity of one or more nucleic acid polymer molecules to control the particle beam instrument 64 with respect to individual nucleic acid molecules and/or the substrate (e.g., whether to reposition the substrate to read information from a different position on the substrate, such as a different grid position). It may be desirable to control the particle beam instrument in this manner, for example, to reduce the data and/or time needed to obtain information that one wishes to obtain from use of the instrument.

Controlling the particle beam instrument 64 relative to individual molecules can be done, for example, to reduce the amount of sequence that is determined. In some embodiments, module 71 may be configured to stop sequencing operations after determining only a portion of the sequence, such as if the portion is characteristic of the sequence of the whole nucleic acid polymer. This may be determined by querying the nucleic acid polymer information 88, after which the identity of the sequence may be determined based on the partial sequence.

Optionally, the instrument 64 can be controlled (e.g., through instructions included in feedback information 62) to move to a distal part of the nucleic acid polymer molecule, e.g., skipping the sequencing of a portion of the nucleic acid polymer molecule. Particle beam instrument 64 may be instructed to move to a particular location on the nucleic acid polymer being sequenced. This may be done by physical movement of the beam or by selective data analysis, for example. Data analysis module 71 may determine moving instructions by integrating information about a portion of the sequence that is desired to be confirmed and information about the physical distance away from the portion that is currently being sequenced, such as by calculating the distance based on internucleotide distances. For example, after sequencing the first 100 nucleotides of a nucleic acid polymer, the data analysis module 71 may determine the likelihood that the polymer has a particular sequence over its entire length, e.g., by recognizing a similar or identical sequence in information accessed from data resource 86 (e.g., from nucleic acid polymer information 88). Feedback module 72 then may send feedback information 62 to particle beam instrument 64, indicating that the instrument 64 may skip to another part(s) of the nucleic acid polymer in order to confirm the sequence. This may be particularly useful in distinguishing among allelic nucleic acid sequences. Controlling the particle beam instrument 64 in the foregoing manner may be carried out independently (e.g., automatically) by data analysis module 72 (e.g., module 72 may be configured to do so without human intervention), or may be performed optionally in response to user input. For example, user interface module 82 may be configured to report information to the user as user output 80, and receive instructions from the user as a user input 80.

Controlling the instrument relative to the substrate can be done, for example, to reduce the amount of sequence that is determined and/or the amount of detection and/or identification that is carried out by the system 60. In some embodiments, one may wish to examine only a subset of nucleic acid polymers present on the substrate. For example, if a plurality of gene probes are present on the substrate in a grid pattern (e.g., a microarray), one may examine the positions on the substrate that correspond to only a subset of the gene probes. This may be done, for example, to examine the presence of certain genes that are indicative of a particular disease or set of diseases. If the substrate contains nucleic acid polymers from a subject (e.g., a patient) that is suspected of having a certain condition, then the substrate can be examined for the presence and amount of nucleic acid polymers that correspond to expression of gene sequences that correlate with the condition (or to exclude other conditions) for diagnostic purposes. If the condition is not suspected, one may wish to examine only part of the substrate grid of gene probes until enough data is collected to suggest that the subject has a certain condition, after which other selected parts of the substrate can be examined for confirmation (e.g., if the expression of other genes is expected in the condition).

It should be appreciated that, in some embodiments, at least some aspects of the functionality described herein in relation to data analysis module 71 may be implemented on particle beam instrument 64, detector 68 and/or other components of system 60.

In some embodiments of the invention, the sample exposed to the particle beam instrument may include a plurality of molecules of a same type of nucleic acid polymer. Accordingly, particle beam species resulting from exposing the sample may contain information indicative of the one or more molecules. As a result, the one or more signals 70 may represent information about the plurality of molecules. In such embodiments, the data analysis module may be configured to determine information about a plurality of molecules from the one or more signals 70, and use this information to detect, and/or sequence and/or identify a nucleic acid polymer contained within the sample. For example, the data analysis module may produce a plurality of partial sequences by partially sequencing two or more of the plurality of molecules. The combining modules 76 may be configured to combine the partial sequence to detect, and/or sequence and/or identify the nucleic acid polymer.

In combining partial sequences determined from different molecules, the molecules may be evaluated based on geometry most suited to interpretation. For example, some molecules will have favorable geometry for certain base pairs but not for others. As an example, the positions of nucleotides in a nucleic acid double helix may be aligned favorably or unfavorably relative to the plain of the substrate of the sample or the position of the particle beam. As another example, the multiple nucleic acid molecules of the same type that are analyzed may each have a certain portion of nucleotides and/or labels that are favorably positioned relative to the plain of the substrate or the position of the particle beam. The sequence information of these multiple molecules can be obtained based on the favorable positions of each of the nucleic acid molecules, and then combined to provide a complex sequence of the nucleic acid molecules.

As noted above, the data analysis module 71, and one or more components thereof, may be configured to evaluate information determined from the one or more signals 70 to determine the presence and absence of molecules (or atoms within molecules), a number of molecules present, a sequence of nucleotides or base pairs in nucleic acid molecules, lengths of nucleic acid molecules and shapes of nucleic acid molecules, using any of the techniques described above. Further, any of the information included within the one or more signals 70 or generated from any of the components of data analysis module 71 may be stored in data resource 86, for example, as part of the nucleic acid polymer information 88. Storage module 84 may be configured for this purpose. Further, any of the information included within the one or more signal 70 or determined by any of the modules of data analysis module 71 may be displayed or otherwise communicated to one or more users as part of user input/output 80. User interface module 82 may be configured for this purpose.

System 60 and components thereof, may be implemented using any of a variety of technologies, including software (e.g., C, C#, C++, Java, or a combination thereof), hardware (e.g., one or more application-specific integrated circuits), firmware (e.g., electrically-programmed memory) or any combination thereof. One or more of the components of system 60 may reside on a single device (e.g., a computer), or one or more components may reside on separate, discrete devices. Further, each component may be distributed across multiple devices, and one or more of the devices may be interconnected.

Further, on each of the one or more devices that include one or more components of system 60, each of the components may reside in one or more locations on the system. For example, different portions of the components of these systems may reside in different areas of memory (e.g., RAM, ROM, disk, etc.) on the device. Each of such one or more devices may include, among other components, a plurality of known components such as one or more processors, a memory system, a disk storage system, one or more network interfaces, and one or more busses or other internal communication links interconnecting the various components. System 60 and components thereof, may be implemented using a computer system such as that described below in relation to FIGS. 12 and 13.

One or more of the functions, methods, and acts thereof described above in relation to system 60, and various embodiments and variations of these functions, methods and these acts, individually or in combination, may be defined by computer-readable signals tangibly embodied on one or more computer-readable media, for example, non-volatile recording media, integrated circuit memory elements, or a combination thereof. Computer readable media can be any available media that can be accessed by a computer. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, other types of volatile and non-volatile memory, any other medium which can be used to store the desired information and which can accessed by a computer, and any suitable combination of the foregoing.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, wireless media such as acoustic, RF, infrared and other wireless media, other types of communication media, and any suitable combination of the foregoing.

Computer-readable signals embodied on one or more computer-readable media may define instructions, for example, as part of one or more programs, that, as a result of being executed by a computer, instruct the computer to perform one or more of the functions described herein (e.g., in relation to system 60), and/or various embodiments, variations and combinations thereof. Such instructions may be written in any of a plurality of programming languages, for example, Java, J#, Visual Basic, C, C#, or C++, Fortran, Pascal, Eiffel, Basic, COBOL, etc., or any of a variety of combinations thereof. The computer-readable media on which such instructions are embodied may reside on one or more of the components of either of systems 60 or 90 described herein, may be distributed across one or more of such components, and may be in transition there between.

The computer-readable media may be transportable such that the instructions stored thereon can be loaded onto any computer system resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement the above-discussed aspects of the present invention.

Figure 12:
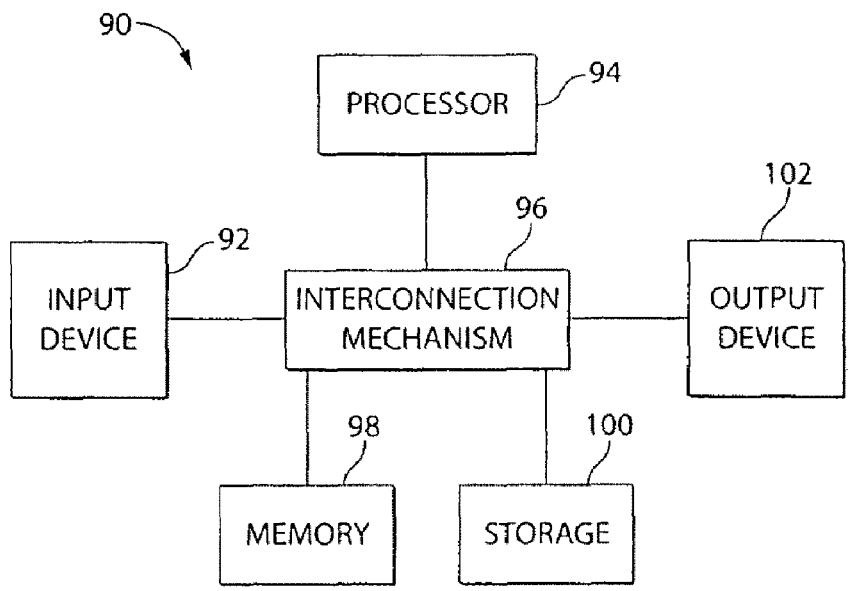
FIG. 12 is a block diagram illustrating a general purpose computer system.
Figure 13:
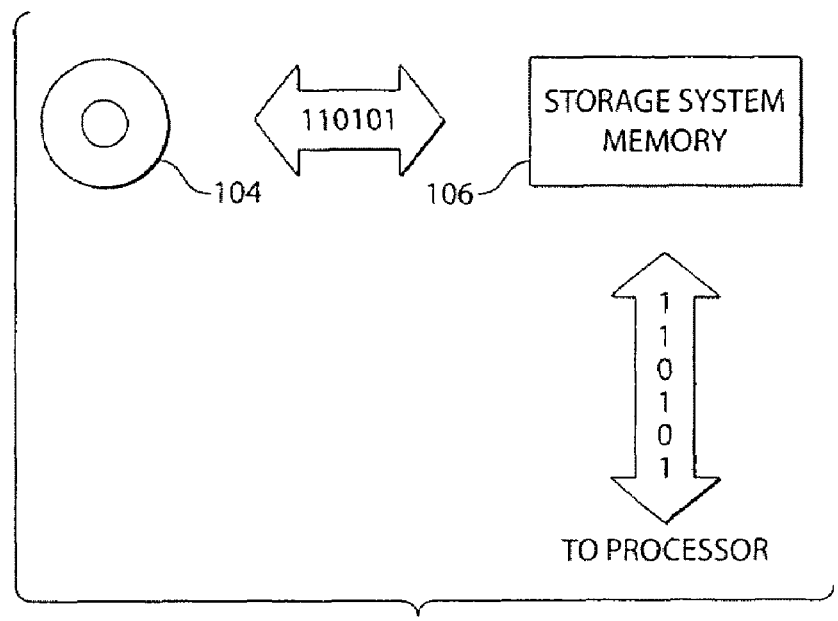
FIG. 13 shows a storage system of the general purpose computer system of FIG. 12.

It should be appreciated that any single component or collection of multiple components of a computer system, for example, the computer system described in relation to FIGS. 11-13, that perform the functions described herein can be generically considered as one or more controllers that control such functions. The one or more controllers can be implemented in numerous ways, such as with dedicated hardware and/or firmware, using a processor that is programmed using microcode or software to perform the functions recited above or any suitable combination of the foregoing.

Various embodiments according to the invention may be implemented on one or more computer systems. These computer systems, may be, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) or any other type of processor. It should be appreciated that one or more of any type of computer system may be used to implement various embodiments of the invention.

A general-purpose computer system according to one embodiment of the invention is configured to perform one or more of the functions described above. It should be appreciated that the system may perform other functions and the invention is not limited to having any particular function or set of functions.

For example, various aspects of the invention may be implemented as specialized software executing in a general-purpose computer system 90 such as that shown in FIG. 12. The computer system 90 may include a processor 94 connected to one or more memory devices 98, such as a disk drive, memory, or other device for storing data. Memory 98 is typically used for storing programs and data during operation of the computer system 90. Components of computer system 90 may be coupled by an interconnection mechanism 96, which may include one or more busses (e.g., between components that are integrated within a same machine) and/or a network (e.g., between components that reside on separate discrete machines). The interconnection mechanism 96 enables communications (e.g., data, instructions) to be exchanged between system components of system 90. Computer system 90 also includes one or more input devices 92, for example, a keyboard, mouse, trackball, microphone, touch screen, and one or more output devices 102, for example, a printing device, display screen, speaker. In addition, computer system 90 may contain one or more interfaces (not shown) that connect computer system 90 to a communication network (in addition or as an alternative to the interconnection mechanism 96.

The storage system 100, shown in greater detail in FIG. 13, typically includes a computer readable and writeable nonvolatile recording medium 104 in which signals are stored that define a program to be executed by the processor or information stored on or in the medium 104 to be processed by the program. The medium may, for example, be a disk or flash memory. Typically, in operation, the processor causes data to be read from the nonvolatile recording medium 104 into another memory 106 that allows for faster access to the information by the processor than does the medium 104. This memory 106 is typically a volatile, random access memory such as a dynamic random access memory (DRAM) or static memory (SRAM). It may be located in storage system 100, as shown, or in memory system 98, not shown. The processor 94 generally manipulates the data within the integrated circuit memory 98, 106 and then copies the data to the medium 104 after processing is completed. A variety of mechanisms are known for managing data movement between the medium 104 and the integrated circuit memory element 98, 106, and the invention is not limited thereto. The invention is not limited to a particular memory system 98 or storage system 100.

The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

Although computer system 90 is shown by way of example as one type of computer system upon which various aspects of the invention may be practiced, it should be appreciated that aspects of the invention are not limited to being implemented on the computer system as shown in FIG. 12. Various aspects of the invention may be practiced on one or more computers having a different architecture or components that that shown in FIG. 12.

Computer system 90 may be a general-purpose computer system that is programmable using a high-level computer programming language. Computer system 90 also may be implemented using specially-programmed, special-purpose hardware. In computer system 90, processor 94 is typically a commercially available processor such as the well-known Pentium class processor available from the Intel Corporation. Many other processors are available. Such a processor usually executes an operating system which may be, for example, the Windows® 95, Windows® 98, Windows NT®, Windows® 2000 (Windows® ME) or Windows® XP operating systems available from the Microsoft Corporation, MAC OS System X available from Apple Computer, the Solaris Operating System available from Sun Microsystems, Linux available from various sources or UNIX available from various sources. Any of a variety of other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that the present invention is not limited to a specific programming language or computer system, and that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects of the invention may be performed on a client-server system that includes components distributed among one or more server systems that perform various functions according to various embodiments of the invention. These components may be executable, intermediate (e.g., IL) or interpreted (e.g., Java) code which communicate over a communication network (e.g., the Internet) using a communication protocol (e.g., TCP/IP).

It should be appreciated that the invention is not limited to executing on any particular system or group of systems, and that the invention is not limited to any particular distributed architecture, network, or communication protocol.

Various embodiments of the present invention may be programmed using an object-oriented programming language, such as SmallTalk, Java, J# (J-Sharp), C++, Ada, or C# (C-Sharp). Other object-oriented programming languages may also be used. Alternatively, functional, scripting, and/or logical programming languages may be used. Various aspects of the invention may be implemented in a non-programmed environment (e.g., documents created in HTML, XML or other format that, when viewed in a window of a browser program, render aspects of a graphical-user interface (GUI)

or perform other functions). Various aspects of the invention may be implemented as programmed or non-programmed elements, or any combination thereof. Further, various embodiments of the invention may be implemented using Microsoft®.NET technology available from Microsoft Corporation.

One advantage provided by certain systems and methods of the invention is that nucleic acid sequencing, detection and/or identification can be done at extremely high speeds. The high speeds and other features of the invention, such as reduced sample manipulation and reduced need for performing chemistry on samples, also can lead to significant reduction in the cost of such analysis. Thus, systems and methods of the invention may make practical obtaining complete or substantial portions of genomes of individual humans for clinical uses (e.g., pharmacogenomics, diagnostics such as disease susceptibility or prognosis) and research uses (e.g., pharmacological research, research into biological processes, and research into the biological process of diseases). Also, it may be possible using embodiments of the invention to perform nucleic acid assays, not just identifying nucleic acids, but also their quantities, with great precision, within individual cells of an organism. This will provide a detailed understanding of how distinct cells function differently.

One example of the foregoing is the use of the methods described herein in conducting microarray-type analysis of gene expression. Similar to conventional microarrays, grids of oligonucleotides (i.e., probes for specific genes or alleles) are provided on a substrate as described above. Nucleic acids that are labeled as described herein are prepared and contacted with the oligonucleotide grid to capture labeled nucleic acid molecules having specific sequences. In these embodiments, the need for labeling each different nucleotide with a unique label is lessened or eliminated, because the data read is not necessarily concerned with sequence (which is specified by the oligonucleotides) but simply can be concerned with determining the number of molecules bound to a specific oligonucleotide probe (i.e., detecting nucleic acid polymers), and/or determining the length of the nucleic acid polymer to identify the nucleic acid polymer. The application of the methods of the invention to microarray-type analysis and quantification of gene expression yields improvements in speed and quantification. Also, due to the ability to count individual nucleic acid molecules bound to the substrate, the methods permit the use of less sample, without amplification, thereby providing a more accurate picture of gene expression levels.

Systems and methods of the invention may also provide very reliable and reproducible data.

The systems and methods of the invention may also physically archive vast amounts of readable nucleic acid sequence data which allows for preservation of genetic data for future reference and verification.

Systems and methods of the invention may also advantageously use very small amounts of sample, for example, it may be possible to determine sequence data from a single molecule.

The following examples are presented for purposes of illustration but are not intended to be limiting.

EXAMPLE 1

This example describes the steps and reagents to make labeled DNA.

Exemplary procedure for making labeled DNA side by side with regular DNA:

1. A desired template was amplified by polymerase chain reaction (PCR) with standard mixture of dNTPs, 30 cycles.

Reagents:
Taq DNA polymerase (New England Biolabs (NEB), Beverly, Mass., catalog #MO267) dNTPs: 5 mM each dNTPs, 20 mM total NTP concentration (NEB, catalog #N0447) NEB supplied buffers, ultra-pure water.
PCR primers, ZSDp200F (TTATCAATTCACGAAACTGC; SEQ ID NO:1) and
ZSDp200R (AATGCACCTTCTAATAATAC; SEQ ID NO:2), 50 µM stock concentration. Primers were produced by Operon Biotechnologies, Huntsville Ala. [ZSDp200F (52-336-000) and ZSDp200R (52-336-000)].

Note: In different experiments alternate sets of PCR primers were used. The combination of ZSDp200F and ZSDp200R yielded a ~200 bp product (SEQ ID NO:3) amplified from an aldolase gene sequence. Another primer pair yielded a ~1000 bp product.

PCR Conditions for Primers "ZSDp200F" and "ZSDp200R"

| | |
|---|---|
| dH20 | 40.4 µl |
| 10X Taq buffer (NEB) | 5.0 µl |
| 5 mM each dNTP | 2.0 µl |
| Forward primer | 1.0 µl |
| Reverse primer | 1.0 µl |
| NEB Taq Polymerase | 0.5 µl |
| Template (<1 ng of DNA) | 0.1 µl |
| | 50.0 µl total volume per reaction. |

The above mix was scaled up 10× to allow for greater amounts of DNA, but PCR volumes were set at 50 µl per reaction in separate tubes.

An MJ Research (Waltham, Mass., subsequently acquired by Bio-Rad Laboratories of Hercules, Calif.) PTC-200 thermal cycler was used to perform the following cycling conditions. The annealing temperature may need to be optimized based on differences in oligonucleotide primers. These conditions were optimized for these primers.
1×—5 min/95° C.
30×—[40 sec/95° C., 40 sec/55° C., 1 min/72° C.]
1×—7 min/72° C.

2. PCR products were passed over a spin column to remove buffers and nucleotides; the DNA PCR product passed through.

Reagents:
Two methods were used
A: Homemade spin columns were made using Sephadex G75-50 Superfine (GE Healthcare, formerly Amersham Biosciences/Pharmacia Biotech). The PCR mixture was allowed to absorb into the resin for 5 seconds, then spun for 60 seconds at 5,000 rpm in a micro-centrifuge at room temperature. The flow was collected. Presumably, the salts, primers and species other than nucleic acids remained in the resin.
B: Qiagen columns were used to remove nucleotides and buffer agents from PCR products following the protocol included with the kit. (QIAquick Gel Extraction Kit #28704).

3. To compare labeled DNA and "standard" DNA, the sample at this point was divided into two new PCR reactions. Sample 1 was set up essentially as above, however the template was in greater concentration. For Sample 2, only one cycle of PCR was done to obtain DNA labeled on one strand only with iodine atoms (tube 2 below).

| Sample 1 | Sample 2 |
| --- | --- |
| Standard dNTP mix (as above) | Alternative dNTP mix (see below) |
| water to adjust volume | water to adjust volume |
| 10x buffer | 10x buffer |
| primers | primers |

Alternative dNTP mix: (example with dCTP+dUTP)
Stock dCTP+dUTP mix was set at 5 mM each because the stock dCTP is 20 mM concentration. The alternative mix is a combination of standard dATP and dGTP together with 5-Iodo dUTP replacing dTTP, and 5-Iodo dCTP replacing the standard dCTP. These nucleoside triphophate analogs are commercially available.

5-Iodo-dCTP
Producer: Sigma-Aldrich, St. Louis, Mo.
Product Number: 1-8361

5-Iodo-dUTP
Producer: Trilink BioTechnologies, San Diego, Calif.
Product Name: DUTP Iodinated 4. After amplification, the PCR products were passed over a new spin column to remove salt, unincorporatted nucleotides, primers as in step 2 above. The samples passing through the column were ready to be analyzed.

Note: A number of other heavy-atom dNTP analogs are available which are compatible with DNA polymerases and can be incorporated into PCR products. These include alpha sulfur versions of dATP (e.g., dATPαS). Another variation on the above procedure is to label both strands. It is possible to include the nucleoside triphosphate analogs in all 30 cycles of PCR as shown in FIG. 10, which was done with a combination of dATPαS and 2-Iodo-dCTP, dTTP and dGTP.

EXAMPLE 2

This example shows preparation of the substrate and attachment of a nucleic acid sample to the prepared substrate.

Amorphous-carbon coated copper grids (Product Number 01822 or 01822-F Supplier: Ted Pella, Inc. of Redding, Calif.) were first cleaned by dipping them into a solution of "anhydrous" acetone that sat for 24 hours over a bed of 2 Angstrom molecular sieve to remove most water. The same acetone solution was used for all cleaning steps.

Grids were then dried in air and plasma treated for 3 minutes. Plasma was generated by applying a high power RF pulse to air under vacuum at 1-4 torr and the power and duration optimized to create a hydrophilic surface without destroying the grid underneath. Plasma treated grids showed significant hydrophilic character.

To reduce these species to hydroxy groups that can readily react with a silane precursor, a grids were immersed for 5 minutes in a dilute solution of 5% $NaBH_4$ by mass in ethanol. Grids were then floated on top of a 3M HCl acid solution to complete the dissociation of the borane intermediate from the grid and neutralize any remaining reactant, leaving behind a hydroxy (—OH) terminated amorphous carbon film.

Grids were cleaned again by dipping in anhydrous acetone for 10-15 seconds, then floated upon a 2% in acetone solution of vinyltriethoxysilane (VTS). Presumably the VTS reacted with the —OH termination to leave a vinylsilane attached via a Si—O—C bond to the surface of the grid.

After removing unreacted VTS with another acetone immersion, a drop of (conc.) atomically labeled DNA in water was placed on the grid and allowed to evaporate, presumably causing combing through the attachment of the atomically labeled DNA to the grid by reaction with the vinyl group and the subsequent recession of the droplet edge aligning the DNA towards the center of the drop.

EXAMPLE 3

Sample preparation and analysis of nucleic acid molecules using an electron beam instrument.

Figure 14:
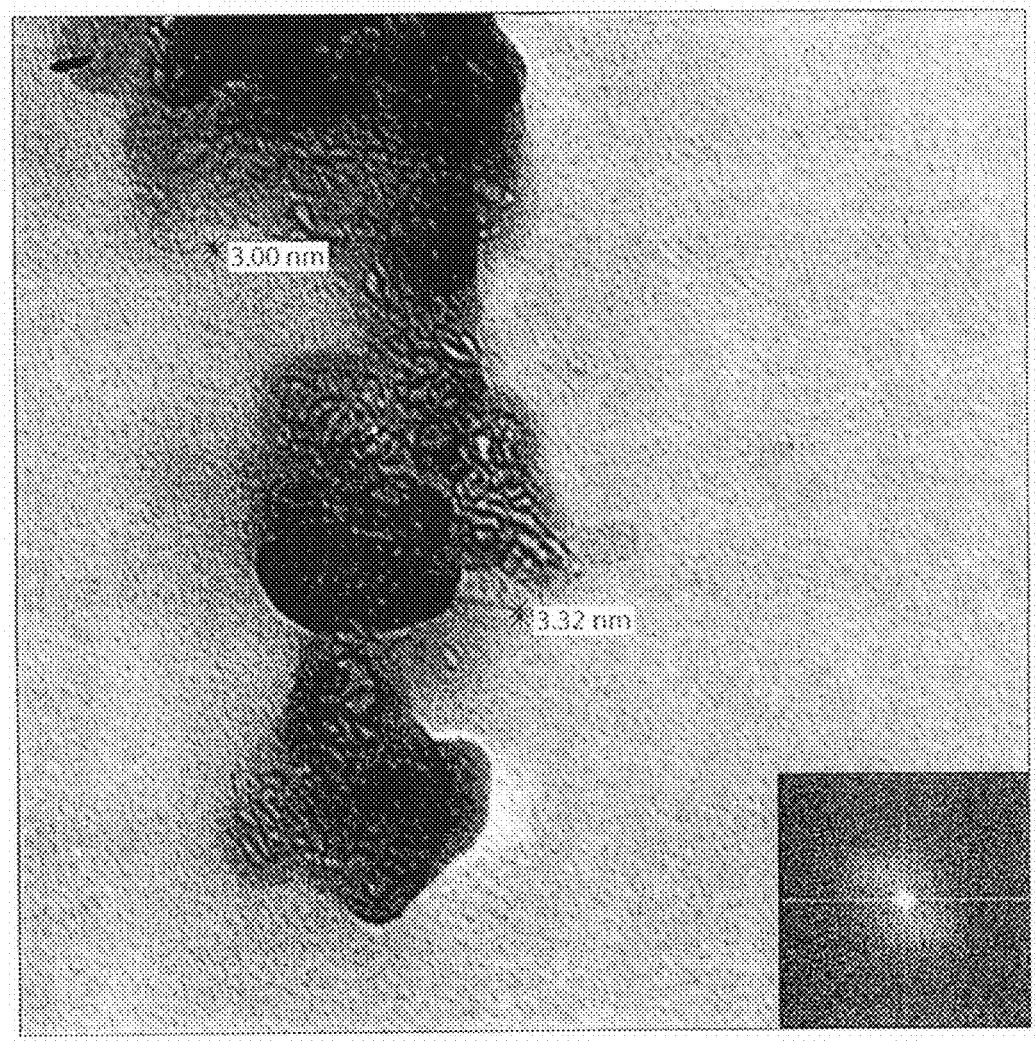
FIG. 14 is a copy of a micrograph showing a labeled DNA strand as described in Example 3.

1. Atomically labeled DNA has been synthesized:
   Using atomically labeled dNTPs only in the last cycle, creating double stranded DNA in which only one strand has atomic label;
   Using atomically labeled dNTPs in all cycles, creating double stranded DNA in which both strands contain labeling atoms; and
   Using atomically labeled dNTPs in the last two cycles, creating a mixture of double stranded DNA in which half of the molecules are labeled in both strands and half are labeled in a single strand.
2. Images of atomically labeled DNA molecules of sufficient resolution and contrast to count and measure molecules have been obtained using an electron beam instrument (TEM):
   From molecules in which both strands are labeled; and
   From molecules in which only one strand is labeled
   A representative image of atomically labeled DNA molecules is shown in FIG. 14. On the image, the atomically labeled DNA molecules are generally circular.

The foregoing were performed with the following instrument:

Instrument:
Manufacturer: JEOL
Headquarters Location: 1-2 Musashino 3-chome Akishima Tokyo 196-8558 Japan
Model: 100S Settings:
Accelerating Voltage: 80 kV
Direct Magnification: 40,000 times
Total Magnification (Scope and Camera): 482,000 times
Camera System and Software: AMT Camera System Alignment Procedures:
Standard Alignment protocol from Lab Manual used. Condensor aperture of 2 selected; Objective Aperture of 2 selected; Focus performed manually rather than with H.V. Wobbler. Final Stigmation performed manually, with FFT (Fast Fourier Transform) of image shown on certain images captured with AMT camera system.

Method Steps:
Sample was prepared from a stock solution of 201 bp PCR amplification product.
The sample was approximately 50 ng/μL of labeled DNA. PCR synthesis was performed with both 5-iodo-dCTP and 5-iodo-dUTP, as described above, providing a single labeling atom per base-pair (all pyrimidines are labeled).
The substrate was exposed to low-pressure plasma to induce hydrophilicity as noted above. A 0.8 to 1.0 μL drop was placed on the treated substrate, and was allowed to evaporate at room temperature and pressure, as described above.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. conducted.

What is claimed is:

1. A method of determining the sequence of a nucleic acid polymer, comprising
forming a complementary strand of the nucleic acid polymer and
identifying a sequence of nucleotides in the nucleic acid polymer and/or in the complementary strand using a particle beam,
wherein the nucleic acid polymer and/or the complementary strand is DNA or RNA.

2. The method of claim 1, wherein the nucleic acid polymer and/or its complementary strand is formed by a nucleic acid polymerase enzyme.

3. The method of claim 1, wherein the complementary strand of the nucleic acid polymer is formed using polymerase chain reaction (PCR).

4. The method of claim 1, wherein the nucleotides of the nucleic acid polymer and/or the complementary strand are modified to include labels.

5. The method of claim 4, wherein the labels are specific for each type of nucleotide.

6. The method of claim 5, wherein nucleotide specific labels are incorporated in the nucleic acid polymer and/or the complementary strand during formation of the nucleic acid polymer and/or the complementary strand.

7. The method of claim 5, wherein nucleotide specific labels are bonded to the nucleotides of the nucleic acid polymer and/or the complementary strand after formation of the nucleic acid polymer and/or the complementary strand.

8. The method of claim 4, wherein the labels comprise one or more atoms.

9. The method of claim 8, wherein the atoms have an atomic number, alone or in aggregate, of greater than 55.

10. The method of claim 8, wherein the atoms have an atomic number, alone or in aggregate, of less than or equal to 55.

11. The method of claim 10, wherein the atoms are halogen atoms.

12. The method of claim 4, wherein the labels comprise three or fewer atoms.

13. The method of claim 12, wherein the labels comprise a single atom.

14. The method of claim 4, wherein the nucleic acid polymer and/or the complementary strand are affixed to a substrate and wherein prior to the step of identification the nucleotides of the nucleic acid polymer and/or its complementary strand are substantially removed from the substrate, leaving the labels of the labeled nucleotides affixed to the substrate.

15. The method of claim 1, wherein the step of identifying a sequence of nucleotides comprises generating a particle beam, exposing the nucleic acid polymer and/or the complementary strand to the particle beam, and identifying the nucleotides due to characteristic changes to the particle beam.

16. The method of claim 15, wherein the nucleotides of the nucleic acid polymer and/or the complementary strand are modified to include labels.

17. The method of claim 15, wherein the step of identifying the nucleotides comprises detecting characteristic changes to the particle beam.

18. The method of claim 1, wherein the particle beam is a lepton beam.

19. The method of claim 18, wherein the lepton beam is an electron beam.

20. The method of claim 1, wherein the nucleic acid polymer and/or the complementary strand are affixed to a substrate.

21. The method of claim 20, wherein the nucleic acid polymer and/or the complementary strand are affixed to a substrate at one end of the nucleic acid polymer and/or the complementary strand, at both ends of the nucleic acid polymer and/or the complementary strand, or at a plurality of locations along the length of the nucleic acid polymer and/or the complementary strand.

22. The method of claim 20, wherein the nucleic acid polymer and/or the complementary strand are substantially straightened prior to identifying the sequence.

23. The method of claim 22, wherein the nucleic acid polymer and/or the complementary strand are straightened by fluid flow;
    optionally wherein the fluid flow comprises molecular combing;
    optionally wherein the fluid comprises one or more liquids, gases, phases or a combination thereof;
    optionally wherein the nucleic acid polymer and/or the complementary strand are attached to a substrate and straightened by hybridization in the fluid flow to oligonucleotides that are attached to the substrate.

24. The method of claim 1, wherein the step of identifying the nucleotides in the nucleic acid polymer and/or its complementary strand comprises interpreting changes in the particle beam resulting from interactions with the nucleotides to detect the nucleotides in the nucleic acid polymer and/or its complementary strand, whereby the sequence of the nucleic acid polymer is determined.

25. The method of claim 24, wherein the nucleotides are labeled.

26. The method of claim 24, wherein the changes in the particle beam are changes in absorbance, reflection, deflection, energy or direction and/or in a spatial pattern.

27. The method of claim 26, wherein the spatial pattern is a one dimensional pattern, a two dimensional pattern or a three dimensional pattern.

28. The method of claim 1, further comprising attaching the complementary strand and/or the nucleic acid polymer to a substrate.

29. The method of claim 28, wherein the attachment is by nucleic acid sequence-specific molecules.

30. The method of claim 29, wherein the nucleic acid sequence-specific molecules are oligonucleotides.

31. The method of claim 28, wherein the substrate is derivatized to provide attachment points that are sequence non-specific.

32. The method of claim 28, wherein the complementary strand and optionally the nucleic acid polymer are attached to the substrate in a grid pattern.

33. The method of claim 1, wherein the step of identifying the sequence of nucleotides comprises performing a plurality of scans of the nucleic acid polymer and/or the complementary strand using the particle beam.

34. The method of claim 33, wherein at least 100 nucleotides are identified in each scan.

35. A method of determining the sequence of a nucleic acid polymer, comprising
    synthesizing the nucleic acid polymer and/or its complementary strand using labeled ribonucleotide and/or deoxyribonucleotide tripho sphates, and
    identifying labeled ribonucleotides and/or deoxyribonucleotides in the nucleic acid polymer and/or its complementary strand using a particle beam,
    wherein the labeled ribonucleotides and/or deoxyribonucleotides, when incorporated in the nucleic acid polymer and/or its complementary strand are identifiable using the particle beam, and
    wherein the nucleic acid polymer and/or the complementary strand of the nucleic acid polymer is DNA or RNA, wherein the nucleic acid polymer and/or its complementary strand is synthesized by a nucleic acid polymerase enzyme or using polymerase chain reaction (PCR).

36. A method of determining the sequence of a nucleic acid polymer, comprising
    synthesizing the nucleic acid polymer and/or its complementary strand using labeled ribonucleotide and/or deoxyribonucleotide triphosphates, and
    identifying labeled ribonucleotides and/or deoxyribonucleotides in the nucleic acid polymer and/or its complementary strand using a particle beam,
    wherein the labeled ribonucleotides and/or deoxyribonucleotides, when incorporated in the nucleic acid polymer and/or its complementary strand are identifiable using the particle beam, and
    wherein the nucleic acid polymer and/or the complementary strand of the nucleic acid polymer is DNA or RNA, wherein the labels are specific for each type of nucleotide, and
    wherein the labels comprise one or more atoms.

37. The method of claim 36, wherein the atoms have an atomic number, alone or in aggregate, of greater than 55.

38. The method of claim 36, wherein the atoms have an atomic number, alone or in aggregate, of less than or equal to 55.

39. The method of claim 38, wherein the atoms are halogen atoms.

40. The method of claim 36,
    wherein nucleotide specific labels are bonded to the nucleotides of the nucleic acid polymer and/or the complementary strand after incorporation of the ribonucleotide and/or deoxyribonucleotide triphosphates into the nucleic acid polymer and/or the complementary strand.

41. A method of determining the sequence of a nucleic acid polymer, comprising
    synthesizing the nucleic acid polymer and/or its complementary strand using labeled ribonucleotide and/or deoxyribonucleotide triphosphates, and
    identifying labeled ribonucleotides and/or deoxyribonucleotides in the nucleic acid polymer and/or its complementary strand using a particle beam,
    wherein the labeled ribonucleotides and/or deoxyribonucleotides, when incorporated in the nucleic acid polymer and/or its complementary strand are identifiable using the particle beam, and
    wherein the nucleic acid polymer and/or the complementary strand of the nucleic acid polymer is DNA or RNA, wherein the nucleic acid polymer and/or the complementary strand are affixed to a substrate, and
    wherein prior to the step of identification the ribonucleotides and/or deoxyribonucleotides of the nucleic acid polymer and/or its complementary strand are substantially removed from the substrate, leaving the labels of the labeled ribonucleotides and/or deoxyribonucleotides affixed to the substrate; or wherein the nucleic acid polymer and/or the complementary strand are affixed to a substrate at both ends of the nucleic acid polymer and/or the complementary strand; or wherein the nucleic acid polymer and/or the complementary strand are affixed to a substrate at a plurality of locations along the length of the nucleic acid polymer and/or the complementary strand.

42. A method of determining the sequence of a nucleic acid polymer, comprising
    synthesizing the nucleic acid polymer and/or its complementary strand using labeled ribonucleotide and/or deoxyribonucleotide triphosphates, and identifying labeled ribonucleotides and/or deoxyribonucleotides in the nucleic acid polymer and/or its complementary strand using a particle beam, wherein the labeled ribonucleotides and/or deoxyribonucleotides, when incorporated in the nucleic acid polymer and/or its complementary strand are identifiable using the particle beam, and wherein the nucleic acid polymer and/or the complementary strand of the nucleic acid polymer is DNA or RNA, wherein the nucleic acid polymer and/or the complementary strand are affixed to a substrate, wherein the nucleic acid polymer and/or the complementary strand are substantially straightened prior to identifying the labeled ribonucleotides and/or deoxyribonucleotides, wherein the nucleic acid polymer and/or the complementary strand are straightened by fluid flow, and wherein the fluid flow comprises molecular combing, and/or wherein the fluid comprises one or more liquids, gases, phases or a combination thereof and/or wherein the nucleic acid polymer and/or the complementary strand are attached to a substrate and straightened by hybridization in a fluid flow to oligonucleotides that are attached to the substrate.

43. The method of claim 42, wherein the changes in the particle beam are changes in absorbance, reflection, deflection, energy or direction, or in a spatial pattern.

44. The method of claim 43, wherein the spatial pattern is a one dimensional pattern, a two dimensional pattern or a three dimensional pattern.

45. A method of determining the sequence of a nucleic acid polymer, comprising synthesizing the nucleic acid polymer and/or its complementary strand using labeled ribonucleotide and/or deoxyribonucleotide triphosphates, and identifying labeled ribonucleotides and/or deoxyribonucleotides in the nucleic acid polymer and/or its complementary strand using a particle beam, wherein the labeled ribonucleotides and/or deoxyribonucleotides, when incorporated in the nucleic acid polymer and/or its complementary strand are identifiable using the particle beam, and wherein the nucleic acid polymer and/or the complementary strand of the nucleic acid polymer is DNA or RNA, further comprising attaching the complementary strand and/or the nucleic acid polymer to a substrate, wherein the attachment is by nucleic acid sequence-specific molecules; or wherein the substrate is derivatized to provide attachment points that are sequence non-specific; or wherein the complementary strand and optionally the nucleic acid polymer are attached to the substrate in a grid pattern; or wherein the step of identifying labeled ribonucleotide and/or deoxyribonucleotide phosphates comprises performing a plurality of scans of the nucleic acid polymer and/or the complementary strand using the particle beam.

46. The method of claim 45, wherein the nucleic acid sequence-specific molecules are oligonucleotides.

47. The method of claim 45, wherein at least 100 nucleotides are identified in each scan.

* * * * *

```
                          SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: oligonucleotide primer

<400> SEQUENCE: 1
ttatcaattc acgaaactgc                                                  20

<210> SEQ ID NO 2
<211> LENGTH: 20
<212> TYPE: DNA
<213> ORGANISM: Artificial
<220> FEATURE:
<223> OTHER INFORMATION: oligonucleotide primer

<400> SEQUENCE: 2
aatgcacctt ctaataatac                                                  20

<210> SEQ ID NO 3
<211> LENGTH: 200
<212> TYPE: DNA
<213> ORGANISM: Unknown
<220> FEATURE:
<223> OTHER INFORMATION: PCR amplification product

<400> SEQUENCE: 3
ttatcaattc acgaaactgc atggggattg gctagatatg catctatttg tcaacaaaat      60
agattagttc caattgttga acctgaaatt ttagctgatg gaccacactc aattgaagtt     120
tgtgcagttg taactcaaaa agttttatca tgtgtattta aagctttaca agaaaatggt     180
gtattattag aaggtgcatt                                                 200

<210> SEQ ID NO 4
<211> LENGTH: 21
<212> TYPE: DNA
<213> ORGANISM: Artificial
<220> FEATURE:
<223> OTHER INFORMATION: oligonucleotide

<400> SEQUENCE: 4
atgcatgcat gcatgcatgc a                                                21

<210> SEQ ID NO 5
<211> LENGTH: 11
<212> TYPE: DNA
<213> ORGANISM: Artificial
<220> FEATURE:
<223> OTHER INFORMATION: oligonucleotide

<400> SEQUENCE: 5
atcgatgcat g                                                           11

<210> SEQ ID NO 6
<211> LENGTH: 11
```

```
-continued

<212> TYPE: DNA
<213> ORGANISM: Artificial
<220> FEATURE:
<223> OTHER INFORMATION: oligonucleotide

<400> SEQUENCE: 6
catgcatcga t                                                            11

<210> SEQ ID NO 7
<211> LENGTH: 11
<212> TYPE: DNA
<213> ORGANISM: Artificial
<220> FEATURE:
<223> OTHER INFORMATION: oligonucleotide

<400> SEQUENCE: 7
atcgatcgat c                                                            11

<210> SEQ ID NO 8
<211> LENGTH: 11
<212> TYPE: DNA
<213> ORGANISM: Artificial
<220> FEATURE:
<223> OTHER INFORMATION: oligonucleotide

<400> SEQUENCE: 8
gatcgatcga t                                                            11
```